(12) United States Patent
Wakabayashi et al.

(10) Patent No.: US 8,740,800 B2
(45) Date of Patent: Jun. 3, 2014

(54) ULTRASONIC TRANSDUCER, METHOD FOR MANUFACTURING ULTRASONIC TRANSDUCER, AND ULTRASONIC ENDOSCOPE

(75) Inventors: Katsuhiro Wakabayashi, Hachioji (JP); Hideo Adachi, Iruma (JP); Mamoru Hasegawa, Nagano (JP); Kazuya Matsumoto, Nagano (JP); Ryo Ohta, Nagano (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 1671 days.

(21) Appl. No.: 11/977,191

(22) Filed: Oct. 24, 2007

(65) Prior Publication Data

US 2008/0200811 A1 Aug. 21, 2008

(30) Foreign Application Priority Data

Oct. 30, 2006 (JP) .................................. 2006-294817

(51) Int. Cl.
*A61B 8/14* (2006.01)
(52) U.S. Cl.
USPC ............ 600/459; 310/334; 310/328; 310/367
(58) Field of Classification Search
USPC ........................... 600/459; 310/334, 328, 367
See application file for complete search history.

(56) References Cited

U.S. PATENT DOCUMENTS

| | | | | |
|---|---|---|---|---|
| 5,329,496 A * | 7/1994 | Smith | ........................... | 367/140 |
| 5,548,564 A * | 8/1996 | Smith | ........................... | 367/140 |
| 5,744,898 A * | 4/1998 | Smith et al. | ................... | 310/334 |
| 6,088,894 A * | 7/2000 | Oakley et al. | ................ | 29/25.35 |
| 6,246,158 B1 * | 6/2001 | Ladabaum | ..................... | 310/334 |
| 6,328,696 B1 * | 12/2001 | Fraser | .......................... | 600/459 |
| 6,396,199 B1 * | 5/2002 | Douglas et al. | ............... | 310/335 |
| 6,443,901 B1 * | 9/2002 | Fraser | .......................... | 600/459 |
| 6,492,762 B1 * | 12/2002 | Pant et al. | ..................... | 310/334 |
| 6,552,471 B1 * | 4/2003 | Chandran et al. | ............. | 310/328 |
| 6,558,330 B1 * | 5/2003 | Ayter et al. | .................... | 600/459 |
| 6,562,650 B2 * | 5/2003 | Ladabaum | ....................... | 438/53 |
| 6,603,240 B1 * | 8/2003 | Kohno et al. | ................. | 310/334 |
| 6,605,043 B1 * | 8/2003 | Dreschel et al. | .............. | 600/459 |

(Continued)

FOREIGN PATENT DOCUMENTS

| | | | |
|---|---|---|---|
| EP | 1 779 784 A1 | 5/2007 |
| EP | 1 810 619 A1 | 7/2007 |

(Continued)

*Primary Examiner* — Long V Le
*Assistant Examiner* — Nicholas Evoy
(74) *Attorney, Agent, or Firm* — Scully, Scott, Murphy & Presser, P.C.

(57) ABSTRACT

An ultrasonic transducer according to the invention includes a flexible sheet, a rigid body portion including a lower electrode made of at least a thin-film conductive material on a surface of the flexible sheet, a dividing portion which divides the rigid body portion into segments, and a plurality of transducer elements including the divided rigid body portion, has at least one transducer cell composed of one of the segments, an insulating partition portion bonded to the segment, an air gap portion surrounded by the partition portion, an upper electrode opposed to the lower electrode extending to the partition portion to sandwich the air gap portion therebetween, and an upper insulating layer formed on the upper electrode, and includes an upper protection film which continuously covers a surface portion of the transducer elements and the dividing portion.

14 Claims, 21 Drawing Sheets

(56) References Cited

U.S. PATENT DOCUMENTS

| | | | | |
|---|---|---|---|---|
| 6,632,178 B1* | 10/2003 | Fraser | | 600/459 |
| 6,656,124 B2* | 12/2003 | Flesch et al. | | 600/459 |
| 6,671,230 B1* | 12/2003 | Benjamin | | 367/155 |
| 6,673,016 B1* | 1/2004 | Bolorforosh et al. | | 600/437 |
| 6,776,762 B2* | 8/2004 | Erikson et al. | | 600/459 |
| 6,809,459 B2* | 10/2004 | Ikeda et al. | | 310/323.11 |
| 6,836,020 B2 | 12/2004 | Cheng et al. | | |
| 6,859,984 B2* | 3/2005 | Dinet et al. | | 29/25.35 |
| 6,894,425 B1* | 5/2005 | Solomon et al. | | 310/334 |
| 6,915,547 B2* | 7/2005 | Takeuchi et al. | | 29/25.35 |
| 6,936,008 B2* | 8/2005 | Tarakci et al. | | 600/437 |
| 6,938,311 B2* | 9/2005 | Tanielian | | 29/25.35 |
| 6,971,148 B2* | 12/2005 | Mohr et al. | | 29/25.35 |
| 6,992,421 B2* | 1/2006 | Ikeda et al. | | 310/328 |
| 6,996,883 B2* | 2/2006 | Chandran et al. | | 29/25.35 |
| 7,332,850 B2* | 2/2008 | Ladabaum et al. | | 310/334 |
| 7,512,038 B2* | 3/2009 | Machida et al. | | 367/181 |
| 7,530,151 B2* | 5/2009 | Osawa | | 29/25.35 |
| 7,576,475 B2* | 8/2009 | Izumi et al. | | 310/328 |
| 7,589,455 B2* | 9/2009 | Adachi et al. | | 310/335 |
| 7,696,671 B2* | 4/2010 | Sawada et al. | | 310/334 |
| 7,779,531 B2* | 8/2010 | Ladabaum et al. | | 29/594 |
| 7,872,949 B2* | 1/2011 | Osawa | | 367/189 |
| 2004/0000847 A1* | 1/2004 | Ladabaum et al. | | 310/367 |
| 2006/0075818 A1 | 4/2006 | Huang et al. | | |
| 2009/0115291 A1* | 5/2009 | Osawa | | 310/336 |

FOREIGN PATENT DOCUMENTS

| | | |
|---|---|---|
| JP | 2006-26232 | 2/2006 |
| JP | 2006-122188 | 5/2006 |
| JP | 2006-166985 | 6/2006 |
| WO | WO 03/035281 | 5/2003 |
| WO | WO 2005/120355 A1 | 12/2005 |
| WO | WO 2006/046471 A1 | 5/2006 |

* cited by examiner

ULTRASONIC TRANSDUCER, METHOD FOR MANUFACTURING ULTRASONIC TRANSDUCER, AND ULTRASONIC ENDOSCOPE

This application claims benefit of Japanese Application No. 2006-294817 filed on Oct. 30, 2006, the contents of which are incorporated by this reference.

BACKGROUND OF THE INVENTION

1. Field of the Invention

The present invention relates to a micromachined capacitive ultrasonic transducer which is manufactured by processing a semiconductor substrate using a micromachining process, a method for manufacturing the ultrasonic transducer, and an ultrasonic endoscope including the ultrasonic transducer in an ultrasonic transmitting and receiving portion.

2. Description of the Related Art

An ultrasonic diagnostic method for applying an ultrasound into a body and visualizing and diagnosing a state in the body from an echo signal of the ultrasound has recently become widespread. Examples of a medical device used for the ultrasonic diagnostic method include an ultrasonic echo device which can visualize a state in a body from a surface of the body and an ultrasonic endoscope which includes an ultrasonic transducer portion for transmitting and receiving an ultrasound at a distal end portion and can be inserted into a body cavity and visualize a state in the body.

Among medical devices for ultrasonic diagnosis, ultrasonic endoscopes are provided with various contrivances for a slimness to improve an ability to be inserted into a body cavity and reduce pain of a patient. For this reason, ultrasonic transducer portions become smaller in size and are provided with various contrivances for a size reduction.

Such a conventional ultrasonic transducer used in an ultrasonic endoscope may contain lead. With recent environmental issues, there is a call for an ultrasonic transducer, provided in an ultrasonic endoscope which is inserted into a body when used, to be lead-free.

It is preferable to use a c-MUT (Capacitive Micromachined Ultrasonic Transducer: including capacitive micromachined ultrasonic probe) as disclosed in, e.g., U.S. Pat. No. 6,836,020 B2 as an ultrasonic transducer whose downsizing can be achieved without using lead.

As another example, an electrostatic type transducer formed on a multi-layered printed circuit board is disclosed in International Publication WO 2003/035281 A2. The electrostatic type transducer has gas pockets serving as air gap portions obtained by forming scratches and pits in an electrode portion. Note that in a technique in International Publication WO 2003/035281 A2, a conductive through hole is formed in a multi-layered rigid substrate or flexible printed circuit board, and a backplate electrode in which gas pockets are formed instead of air gap portions is provided in a roughened backplate.

SUMMARY OF THE INVENTION

According to the present invention, there is provided an ultrasonic transducer comprising a flexible sheet, a rigid body portion including a lower electrode which is made of at least a thin-film conductive material on a surface of the flexible sheet, a dividing portion which divides the rigid body portion into a plurality of rigid body portion segments separated from each other, and a plurality of transducer elements including the rigid body portion divided by the dividing portion, wherein the ultrasonic transducer has at least one transducer cell composed of one of the rigid body portion segments, an insulating partition portion bonded to the rigid body portion segment, an air gap portion surrounded by the partition portion, an upper electrode opposed to the lower electrode which is formed to extend to the partition portion to sandwich the air gap portion therebetween, and an upper insulating layer formed on the upper electrode and comprises an upper protection film which continuously covers a surface portion on the side of the upper electrode of the plurality of transducer elements and the dividing portion.

According to the present invention, there is also provided a method for manufacturing an ultrasonic transducer, wherein the ultrasonic transducer is formed using a micromachining technique, and the method comprises forming a plurality of transducer elements, each comprising a pair of electrodes, formed on a surface of a rigid substrate on which an insulating layer is formed, coating surfaces of the plurality of transducer elements with a flexible member to form a sheet, and forming a groove portion from one side of the substrate such that the plurality of transducer elements are spaced apart from each other by a predetermined distance and are coupled by the sheet, after removing a rigid member of the substrate.

According to the present invention, there is further provided an ultrasonic endoscope comprising an ultrasonic transducer which is arranged on a distal end side of a distal end rigid portion constituting a distal end of an endoscope insertion portion and in which at least one ultrasonic transducer unit is arrayed, wherein each of the at least one ultrasonic transducer unit comprises a plurality of transducer elements, each having at least one transducer cell including a pair of electrodes, a flexible sheet on which the plurality of transducer elements are arrayed, and a dividing portion for separating the plurality of transducer elements such that the plurality of transducer elements are spaced apart from each other by a predetermined distance.

The above and other objects, features and advantages of the invention will become more clearly understood from the following description referring to the accompanying drawings.

DETAILED DESCRIPTION OF THE PREFERRED EMBODIMENTS

In conventional c-MUT structures, silicon substrates with a thickness of about 200 μm or more are used to improve handling. For this reason, in a conventional c-MUT structure, a through hole is formed in a silicon substrate, an electric wiring structure for application (of a signal) to and return from (grounding of) a pair of electrodes becomes complicated, and a dimension in a thickness direction increases. This inhibits a slimness.

In such a conventional c-MUT structure, if an ultrasonic transducer portion is formed by arraying a plurality of transducer elements, vibrations propagate between the transducer elements formed on a rigid substrate to inhibit generation of desired ultrasonic vibrations in a scanning area. More specifically, in the conventional c-MUT structure, so-called crosstalk caused by interference between vibrations from the transducer elements makes it difficult to apply ultrasonic vibrations to the scanning area with high precision, and a captured image may be adversely affected.

If a conventional transducer element is used in a medical device such as an ultrasonic endoscope to be inserted into a body, a size reduction is desired to be achieved for a reduction in pain of a patient, a reduction in invasiveness, and the like.

Under the circumstances, techniques according to embodiments to be described below reduce crosstalk caused by interference between vibrations of c-MUT, increase resolution, and allow a size reduction.

Embodiments of the present invention will be described below with reference to the drawings. Note that each embodiment of the present invention will be described taking an ultrasonic endoscope which is a medical device as an example.

(First Embodiment)

Figure 1:
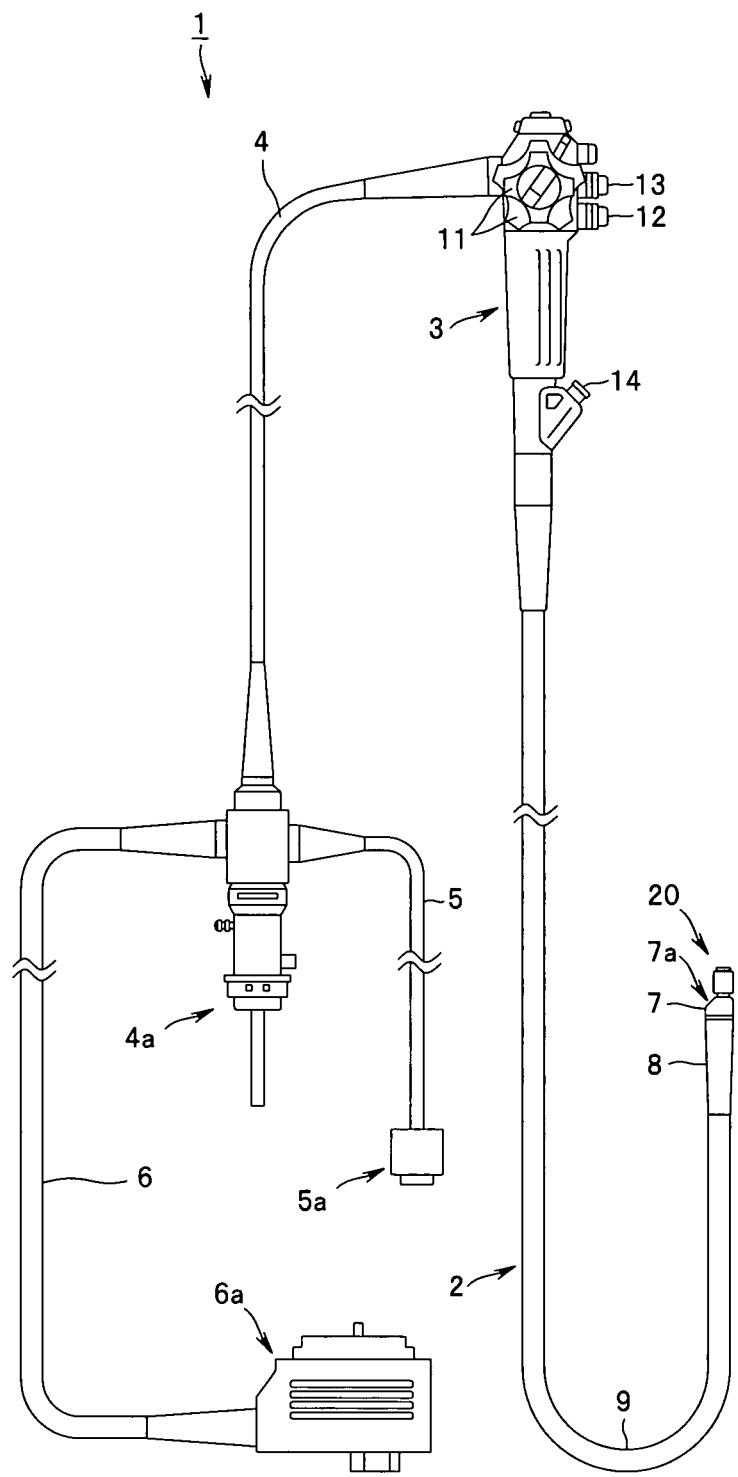
FIG. 1 is a view for explaining a schematic configuration of an ultrasonic endoscope according to a first embodiment.
Figure 2:
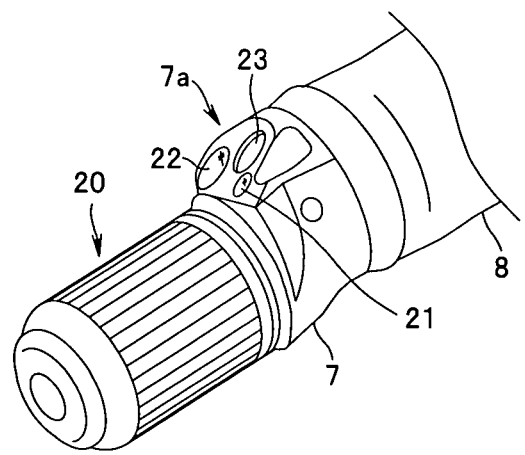
FIG. 2 is a view for explaining a schematic configuration of a distal end portion of the ultrasonic endoscope in the first embodiment.
Figure 3:
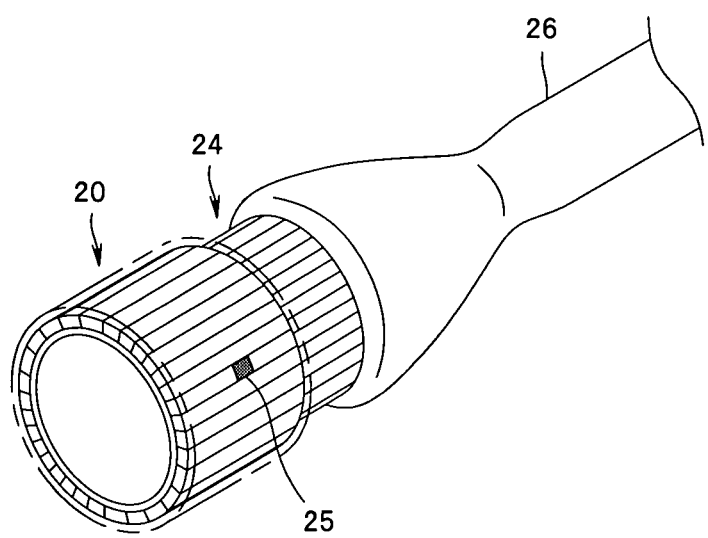
FIG. 3 is a view for explaining a configuration of an ultrasonic transducer portion in the first embodiment.
Figure 4:
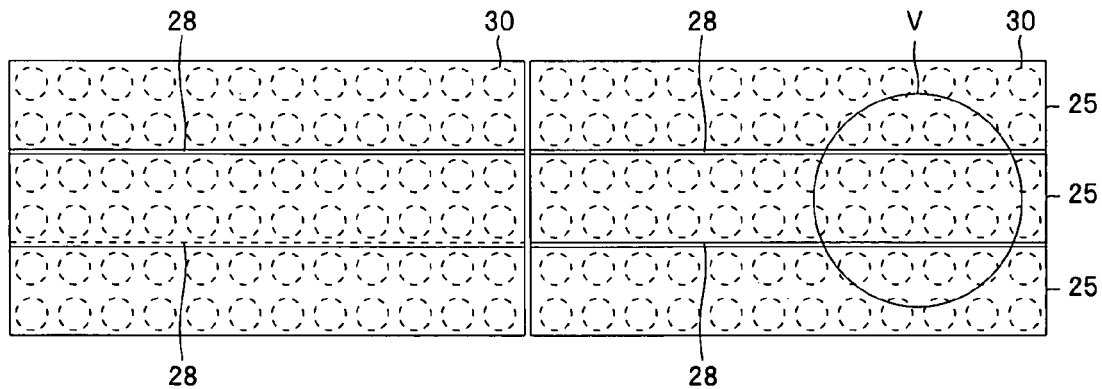
FIG. 4 is a top view of an ultrasonic transducer in the first embodiment.
Figure 5:
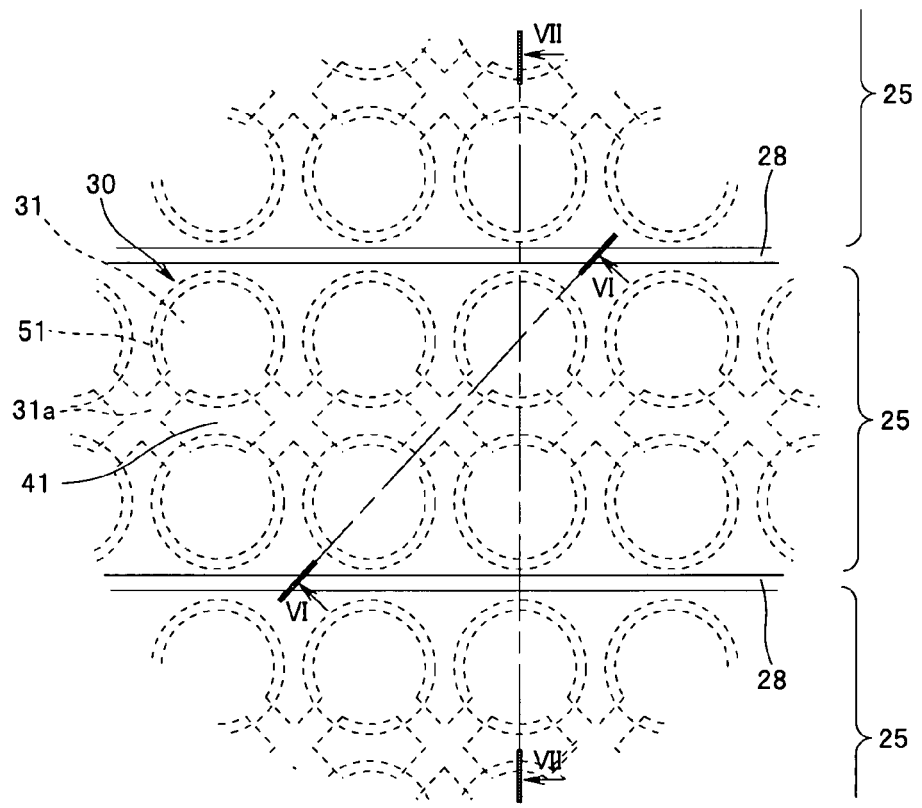
FIG. 5 is an enlarged view of a circle V in FIG. 4 in the first embodiment.
Figure 6:
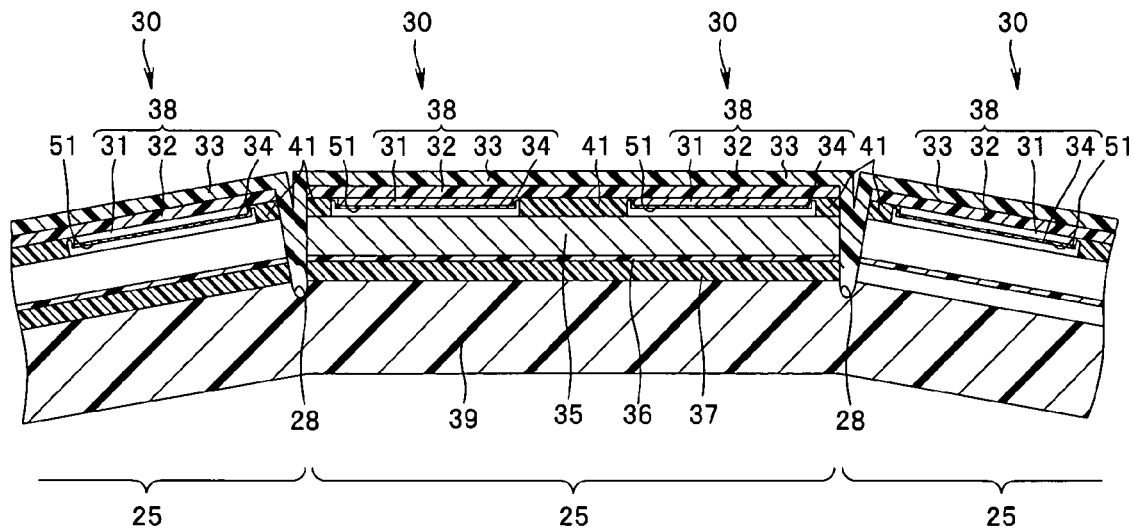
FIG. 6 is a cross-sectional view of c-MUT cells taken along line VI-VI in FIG. 5 in the first embodiment.
Figure 7:
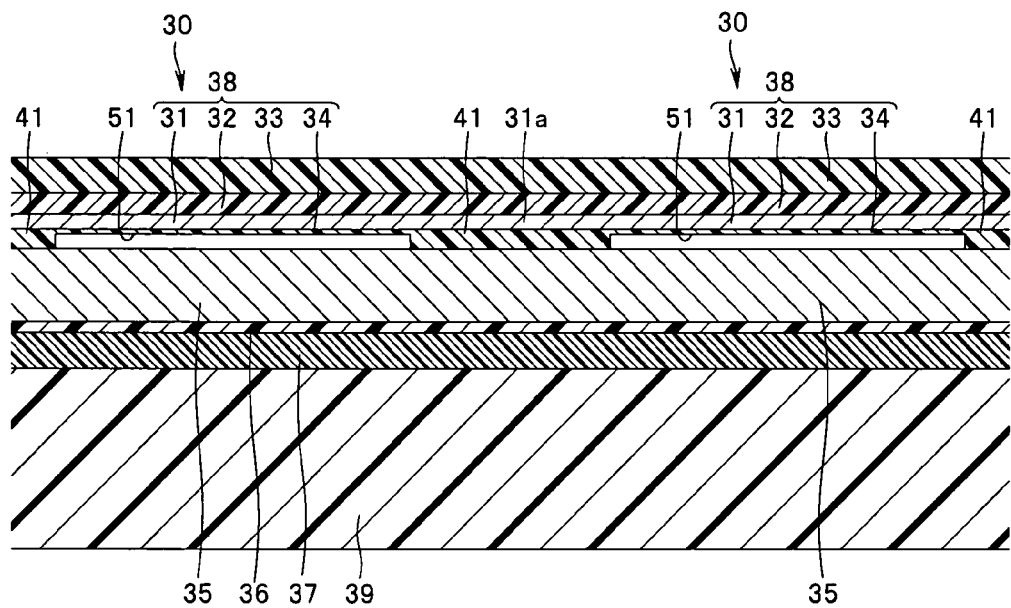
FIG. 7 is a cross-sectional view of c-MUT cells taken along line VII-VII in FIG. 5 in the first embodiment.
Figure 8:
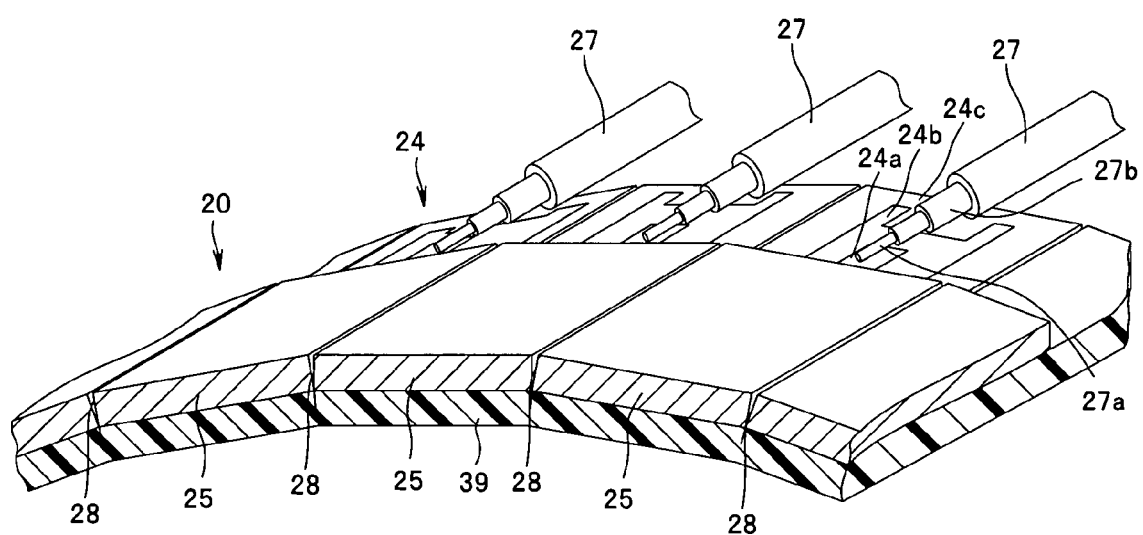
FIG. 8 is a perspective view for explaining a configuration of a cable connection board portion to which coaxial cables are connected in the first embodiment.
Figure 9:
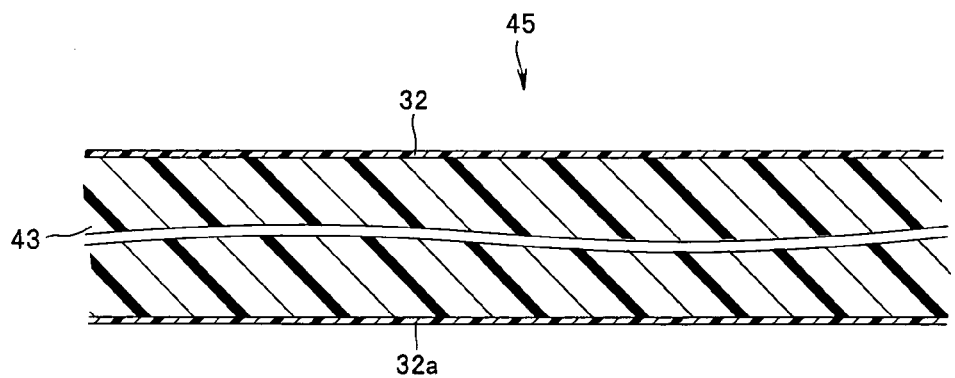
FIG. 9 is a cross-sectional view showing a thick oxide film-coated wafer in the first embodiment.
Figure 10:
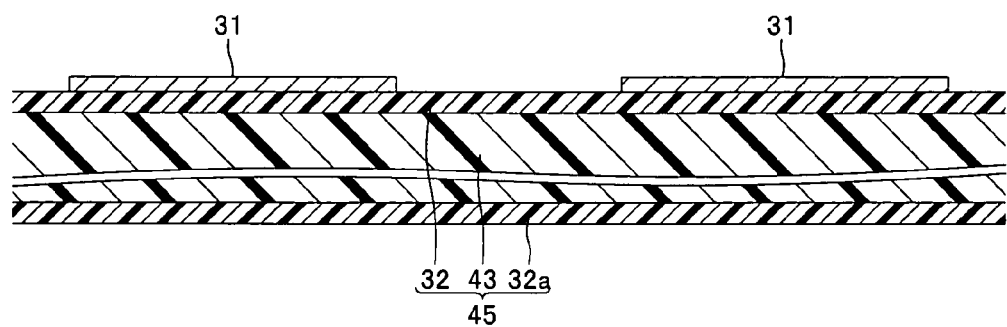
FIG. 10 is a cross-sectional view showing a state in which upper electrodes are formed on the thick oxide film-coated wafer in the first embodiment.
Figure 11:
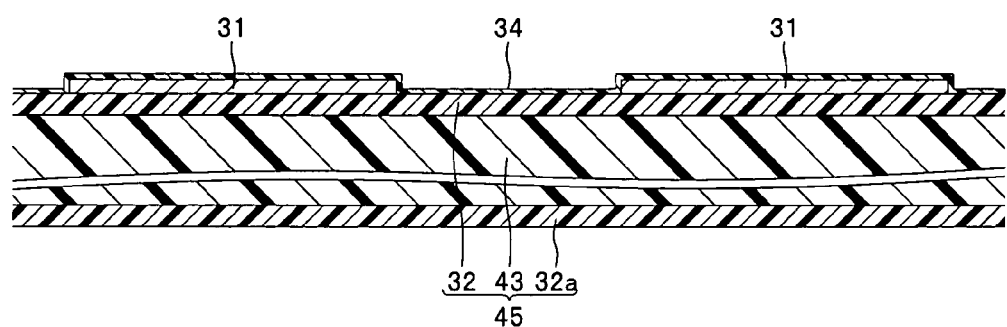
FIG. 11 is a cross-sectional view showing the thick oxide film-coated wafer with a first insulating film formed in the first embodiment.
Figure 12:
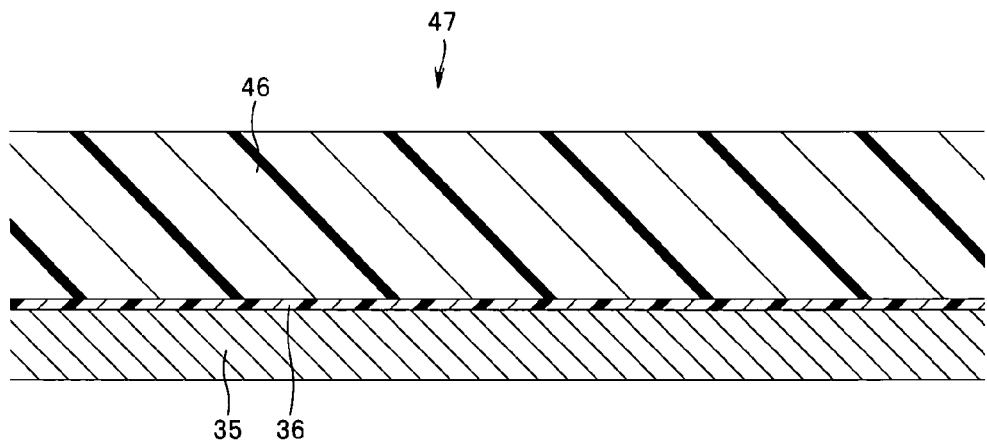
FIG. 12 is a cross-sectional view showing an SOI wafer in the first embodiment.
Figure 13:
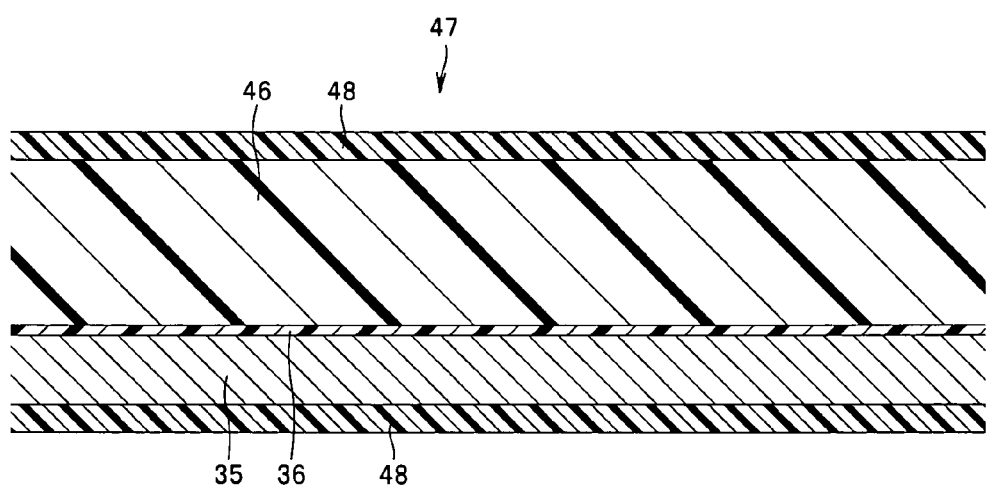
FIG. 13 is a cross-sectional view showing a state in which silicon oxide films are formed on the SOI wafer in the first embodiment.
Figure 14:
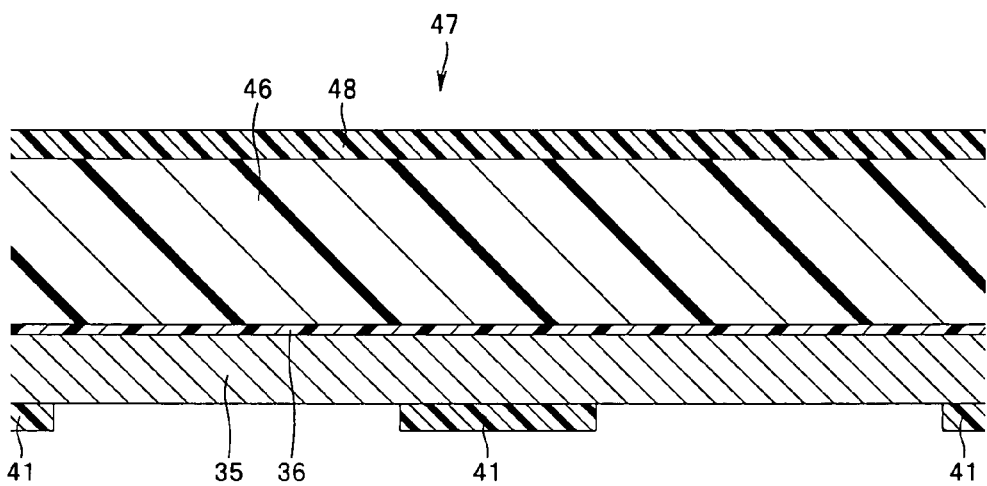
FIG. 14 is a cross-sectional view showing the SOI wafer with the silicon oxide film on a lower electrode etched in the first embodiment.
Figure 15:
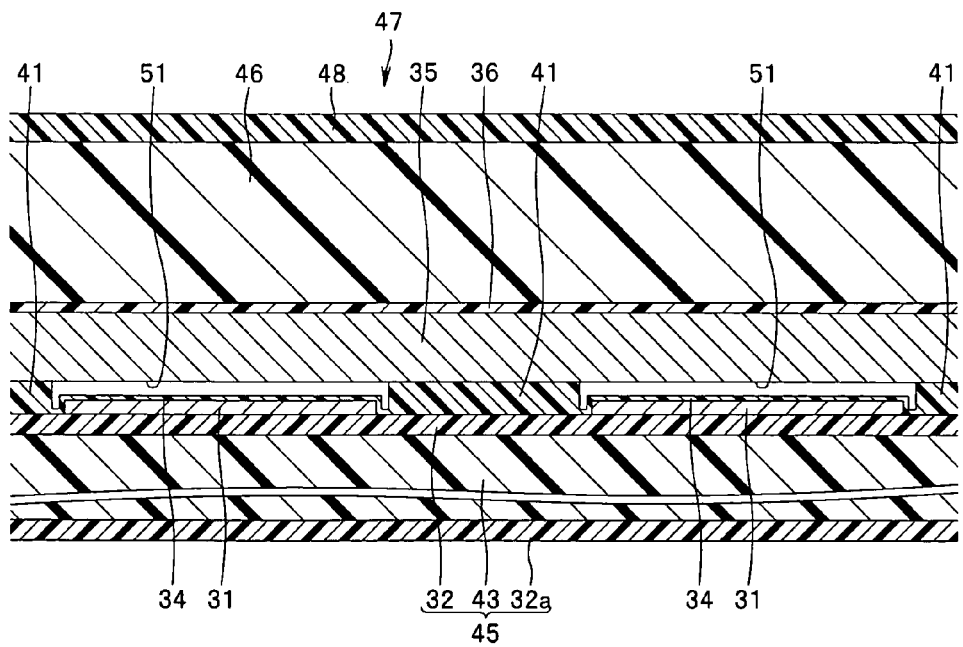
FIG. 15 is a cross-sectional view showing a part of a process of manufacturing a c-MUT cell in a state in which the thick oxide film-coated wafer and SOI wafer are bonded in the first embodiment.
Figure 16:
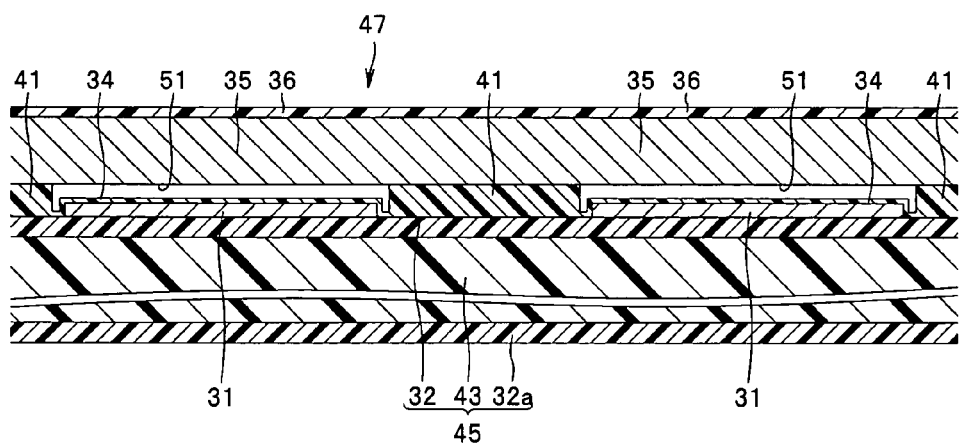
FIG. 16 is a cross-sectional view showing a part of the process of manufacturing a c-MUT cell in a state in which a base silicon portion of the SOI wafer is etched and removed in the first embodiment.
Figure 17:
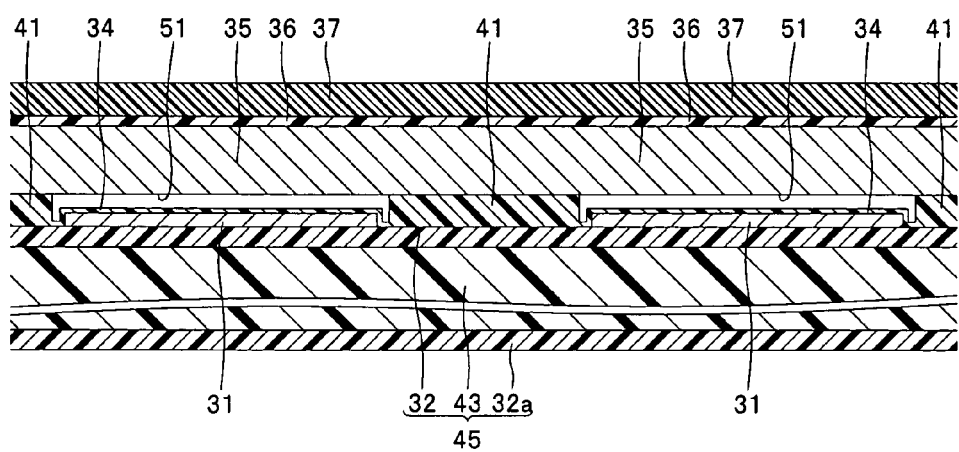
FIG. 17 is a cross-sectional view showing a part of the process of manufacturing a c-MUT cell in a state in which a protection film is formed on an upper surface in the first embodiment.
Figure 18:
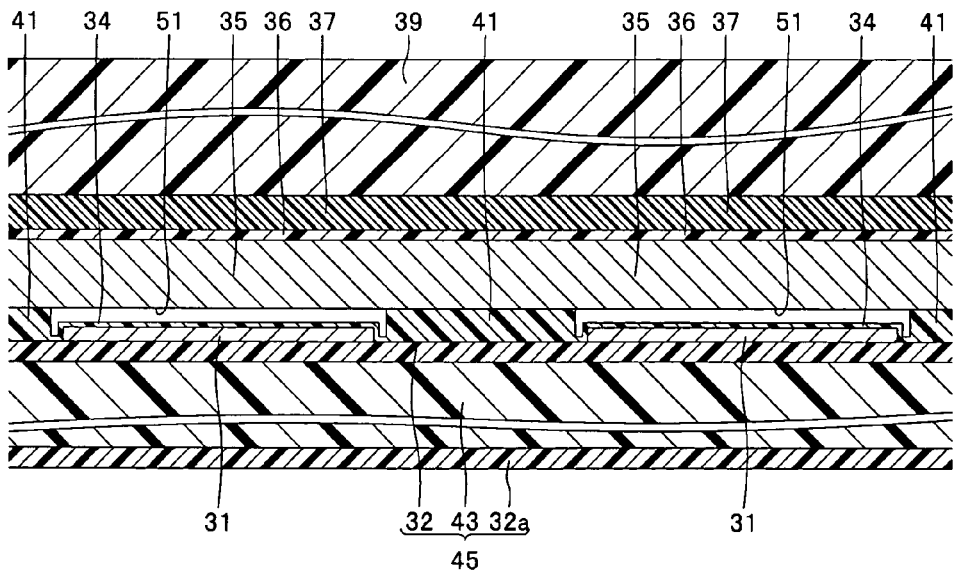
FIG. 18 is a cross-sectional view showing a part of the process of manufacturing a c-MUT cell in a state in which a flexible sheet is formed on the protection film in the first embodiment.
Figure 19:
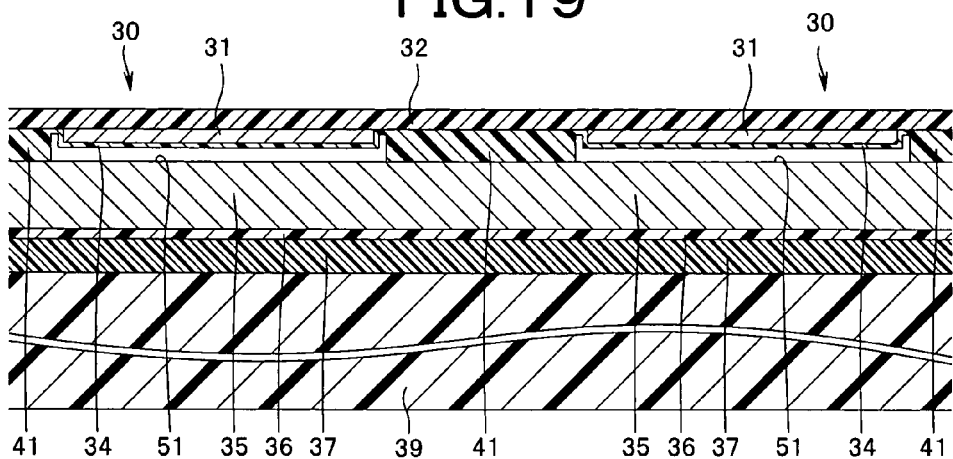
FIG. 19 is a cross-sectional view showing a part of the process of manufacturing a c-MUT cell in a state in which a base silicon portion of the thick oxide film-coated wafer is etched and removed in the first embodiment.
Figure 20:
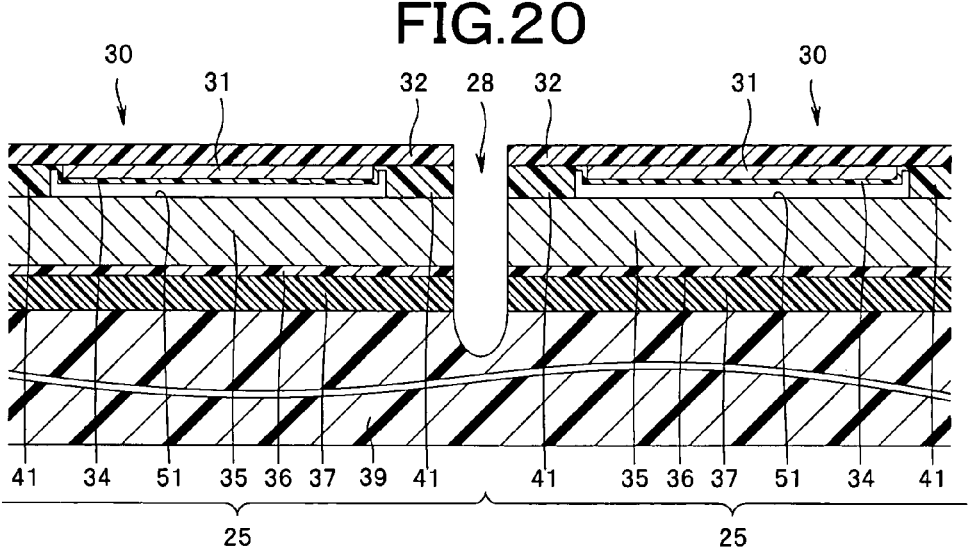
FIG. 20 is a cross-sectional view showing a part of the process of manufacturing a c-MUT cell in a state in which an inter-cell-group etching groove is formed in the first embodiment.
Figure 21:
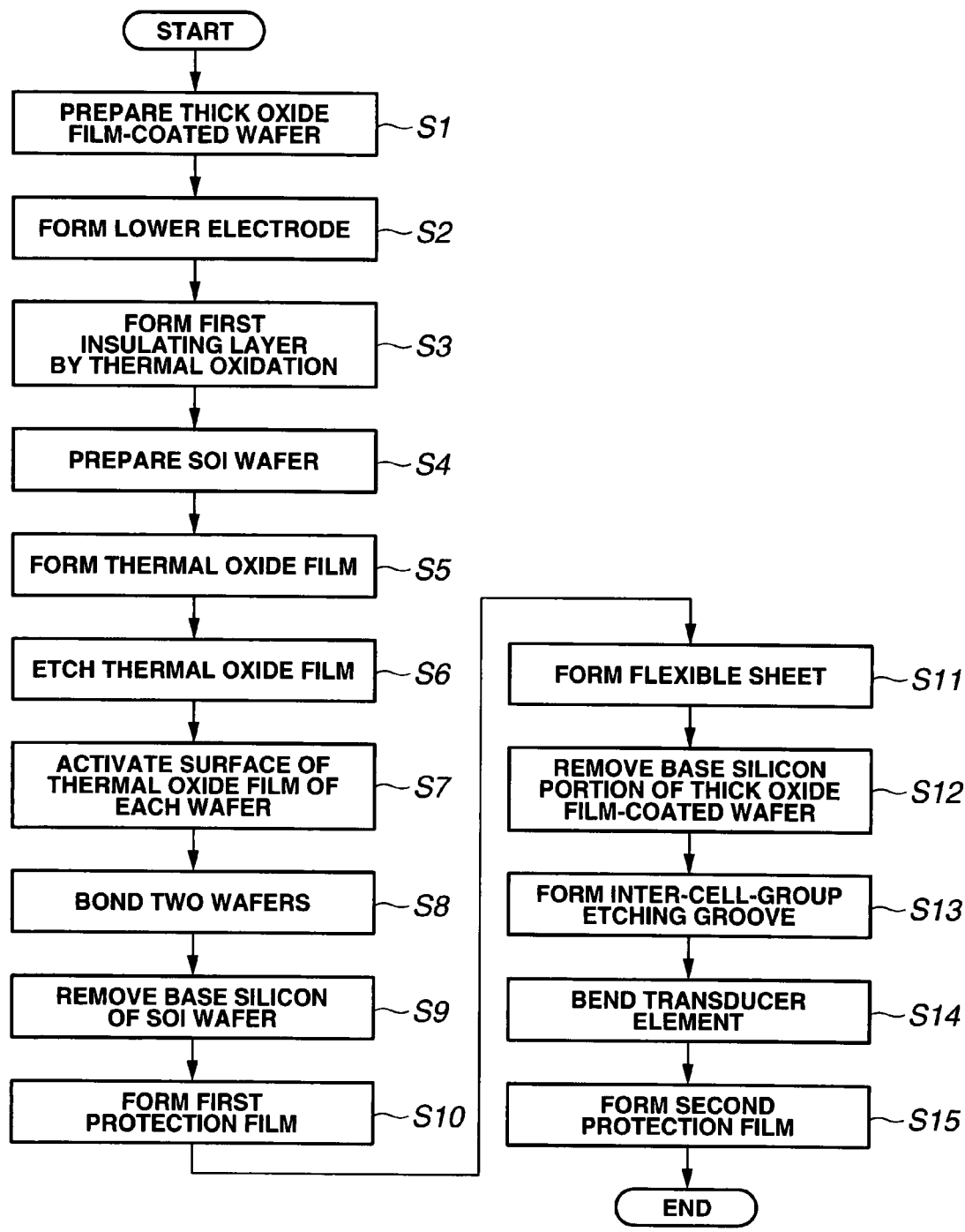
FIG. 21 is a flow chart showing steps in manufacturing a c-MUT cell in the first embodiment.

FIGS. 1 to 21 show a first embodiment of the present invention. FIG. 1 is a view for explaining a schematic configuration of an ultrasonic endoscope. FIG. 2 is a view for explaining a schematic configuration of a distal end portion of the ultrasonic endoscope. FIG. 3 is a view for explaining a configuration of an ultrasonic transducer portion. FIG. 4 is a top view of an ultrasonic transducer. FIG. 5 is an enlarged view of a circle V in FIG. 4. FIG. 6 is a cross-sectional view of c-MUT cells taken along line VI-VI in FIG. 5. FIG. 7 is a cross-sectional view of c-MUT cells taken along line VII-VII in FIG. 5. FIG. 8 is a perspective view for explaining a configuration of a cable connection board portion to which coaxial cables are connected. FIG. 9 is a cross-sectional view showing a thick oxide film-coated wafer. FIG. 10 is a cross-sectional view showing a state in which upper electrodes are formed on the thick oxide film-coated wafer. FIG. 11 is a cross-sectional view showing the thick oxide film-coated wafer with a first insulating film formed. FIG. 12 is a cross-sectional view showing an SOI wafer. FIG. 13 is a cross-sectional view showing a state in which silicon oxide films are formed on the SOI wafer. FIG. 14 is a cross-sectional view showing the SOI wafer with the silicon oxide film on a lower electrode etched. FIG. 15 is a cross-sectional view showing a part of a process of manufacturing a c-MUT cell in a state in which the thick oxide film-coated wafer and SOI wafer are bonded. FIG. 16 is a cross-sectional view showing a part of the process of manufacturing a c-MUT cell in a state in which a base silicon portion of the SOI wafer is etched and removed. FIG. 17 is a cross-sectional view showing a part of the process of manufacturing a c-MUT cell in a state in which a protection film is formed on an upper surface. FIG. 18 is a cross-sectional view showing a part of the process of manufacturing a c-MUT cell in a state in which a flexible sheet is formed on the protection film. FIG. 19 is a cross-sectional view showing a part of the process of manufacturing a c-MUT cell in a state in which a base silicon portion of the thick oxide film-coated wafer is etched and removed. FIG. 20 is a cross-sectional view showing a part of the process of manufacturing a c-MUT cell in a state in which an inter-cell-group etching groove is formed. FIG. 21 is a flow chart showing steps in manufacturing a c-MUT cell.

As shown in FIG. 1, an ultrasonic endoscope 1 according to the present embodiment is mainly composed of a slender insertion portion 2 to be inserted into a body, an operation portion 3 located at a proximal end of the insertion portion 2, and a universal cord 4 extending from a side of the operation portion 3.

An endoscope connector 4a to be connected to a light source device (not shown) is provided at a proximal end portion of the universal cord 4. An electric cable 5 to be detachably connected to a camera control unit (not shown) via an electric connector 5a and an ultrasonic cable 6 to be detachably connected to an ultrasonic observation device (not shown) via an ultrasonic connector 6a are extending from the endoscope connector 4a.

The insertion portion 2 is composed of a distal end rigid portion 7 made of a hard resin member, a bendable bending portion 8 located at a rear end of the distal end rigid portion 7, and a thin and long flexible tube portion 9 located at a rear end of the bending portion 8 and leading to a distal end portion of the operation portion 3 which are provided to be continuous in order from a distal end side of the insertion portion 2. An ultrasonic transducer portion 20 which is an ultrasonic transmitting and receiving portion having a plurality of arrayed ultrasonic transducers of an electronic scanning type for transmitting and receiving an ultrasound is provided on a distal end side of the distal end rigid portion 7.

Note that a polysulfone with high chemical resistance or high biocompatibility is used as a material for the distal end rigid portion 7. An angle knob 11 for controlling to bend the bending portion 8 in a desired direction, an air-supply/water-supply button 12 for performing air supply and water supply operation, a suction button 13 for performing suction operation, a treatment-instrument insertion port 14 serving as an inlet for a treatment instrument introduced into a body cavity, and the like are provided in the operation portion 3.

As shown in FIG. 2, an illumination lens cover 21 constituting an illumination optical system, an observation lens cover 22 constituting an observation optical system, a forceps port 23 also serving as a suction port, and an air-supply and water-supply nozzle (not shown) are arranged at a distal end surface 7a of the distal end rigid portion 7 having the ultrasonic transducer portion 20.

The ultrasonic transducer portion 20 is an electronic radial type transducer distal end portion which is formed such that a vibration film of a c-MUT (Capacitive Micromachined Ultrasonic Transducer: including capacitive micromachined ultrasonic probe) obtained by processing a silicon substrate using a silicon micromachining technique faces outward and in which a plurality of transducer elements 25, each being a minimum driving unit composed of a plurality of c-MUT cells and having a rectangular surface, are cylindrically arrayed, as shown in FIG. 3.

A cable connection board portion 24 including electrode pads and GND (ground) electrode pads which are electrically connected to the transducer elements 25 is provided to be continuous with a proximal end side of the ultrasonic transducer portion 20. A coaxial cable bundle 26 whose signal lines are electrically connected to the cable connection board portion 24 is provided to extend from the ultrasonic transducer portion 20. The coaxial cable bundle 26 is inserted through the distal end rigid portion 7, bending portion 8, flexible tube portion 9, operation portion 3, universal cord 4, and ultrasonic cable 6 and is connected to the ultrasonic observation device (not shown) via the ultrasonic connector 6a.

Note that electrodes on an active (signal) side of the transducer elements 25 are structured to be individually supplied with electric signals from cables of the coaxial cable bundle 26 and are not electrically connected to each other.

As shown in FIG. 4, each transducer element 25 includes at least one c-MUT cell (in the present embodiment, a plurality of c-MUT cells, hereinafter simply referred to as cells) 30, and the c-MUT cells 30 are arrayed at substantially equal intervals. An inter-cell-group etching groove 28 which is a linear kerf and constitutes a dividing portion is formed between each adjacent two of the transducer elements 25 to isolate groups of a predetermined number of cells 30 from each other. Segments which are separated by the inter-cell-group etching grooves 28 to be spaced apart at a predetermined distance from each other are the transducer elements 25 serving as the minimum driving unit transducers.

Note that each cell 30 serves as a driving unit element including a pair of electrodes, a membrane which is a vibration film, and a cavity 51 which is a substantially discoid air gap formed between the pair of electrodes to have a circular surface shape by a partition portion 41 formed around the pair of electrodes, as will be described later.

Each of lower electrodes 35 which serves as an active electrode of a pair of electrodes according to the present embodiment is a single-piece electrode plate which has a substantially same shape as the surface shape of each transducer element 25. Each of upper electrodes 31 which serves as a GND electrode of the pair of electrodes has a substantially circular surface shape and is electrically connected to the adjacent upper electrode 31 within the corresponding transducer element 25 via a conducting portion 31a. The conducting portions 31a are provided to extend from two points of an edge portion of each upper electrode 31 formed in a discoid shape at an angle of substantially 90° with respect to each other and intersect with the other conducting portions 31a in the present embodiment. Note that each lower electrode 35 may be divided into pieces for the respective cells 30 corresponding to, e.g., the circular surface shapes of the upper electrodes 31.

Structures of sections of the cells 30 taken along lines VI-VI and VII-VII shown in FIG. 5 will be described in detail with reference to FIGS. 6 and 7. Note that FIG. 7 shows only a structure of a section of the two adjacent cells 30.

As shown in FIG. 6, each cell 30 formed in the transducer element 25 according to the present embodiment is mainly composed of the lower electrode 35 formed on a flexible sheet 39 which is a belt-like body having an inner protection film 37 serving as a first protection film and a third insulating layer 36 formed thereon, the upper electrode 31, which is disposed above the lower electrode 35 at a predetermined distance from the lower electrode 35 via the cavity 51 and has an insulating layer (hereinafter sometimes referred to as a second insulating layer) 34 constituting a bonding film formed at a surface thereof, an insulating layer (hereinafter sometimes referred to as a first insulating layer) 32 which is an upper insulating layer formed on the upper electrode 31, and an exterior protection film 33 which is a second protection film formed on the insulating layer 32 and upper protection film. In the present embodiment, as for the terms "upper" and "lower," the side of an ultrasonic scanning area in generated ultrasonic vibrations is regarded as an upper side.

In the cell 30 according to the present embodiment, the upper electrode 31, first insulating layer 32, exterior protection film 33, and second insulating layer 34 constitute a membrane 38 which is a vibration film. The cavity 51 described above is a vacuum air gap portion (vacuum cavity) which is sealed vertically with the second insulating layer 34 and lower electrode 35 and circumferentially with the partition portion 41 and serves as a damping layer for the membrane 38 in the present embodiment. Note that the lower electrode 35, third insulating layer 36, and inner protection film 37 constitute a rigid body portion of the present embodiment.

As shown in FIG. 7, the upper electrode 31 of each cell 30 within one transducer element 25, and the upper electrode 31 of the adjacent cell 30 are successively and integrally formed via the conducting portion 31a and are electrically connected. The first insulating layer 32 and second insulating layer 34 are also formed on upper and lower surfaces of the conducting portion 31a.

In the present embodiment, the flexible sheet 39 is made of, for example, a polyimide (PI) film with a thickness of 20.0 μm. The first inner protection film 37 formed on the flexible sheet 39 is made of, for example, a silicon nitride (SiN) film with a thickness of 1.0 μm.

The third insulating layer 36 formed on the first inner protection film 37 is made of, for example, a thermal silicon oxide film (e.g., a silicon dioxide ($SiO_2$) film) with a thickness of 0.3 μm. The lower electrode 35 formed on the third insulating layer 36 is made of, for example, a film of low-resistivity silicon (Si) having conductivity with a thickness of 2.0 μm.

The cavity 51 described above is, for example, a substantially cylindrical (substantially discoid) air gap portion which is set to have a diameter φ of 40 μm and a height of 0.4 μm. The partition portion 41 forming an outer periphery of the cavity 51 formed on the lower electrode 35 is made of a silicon dioxide ($SiO_2$) film formed by thermal oxidation. The second insulating layer 34, which forms an upper surface portion of the cavity 51 and covers a lower surface of the upper electrode 31 to keep the upper electrode 31 insulated from the lower electrode 35, is made of, for example, a silicon dioxide ($SiO_2$) film with a thickness of 0.15 μm which is a same material as the material for the partition portion 41.

The upper electrode 31 formed on the second insulating layer 34 is made of an electrically conductive metal or semiconductor or the like, and, for example, a platinum (Pt) film with a thickness of 0.4 μm is used as a material for the upper electrode 31 in the present embodiment. Note that the electrically conductive material for forming the upper electrode 31 is not limited to platinum (Pt) and may be molybdenum (Mo) or titanium (Ti). Also note that the material may be aluminum (Al), which is a low-melting metal, or the like if a manufacturing process has no high-temperature processing step. The conducting portion 31a formed integrally with the upper electrode 31 is made of a same material as the material for the upper electrode 31.

The first insulating layer 32 formed on the upper electrode 31 is made of, for example, a silicon dioxide ($SiO_2$) film which is a thermal oxide film with a thickness of 1.5 μm. The exterior protection film 33 is formed to a thickness of, e.g., 1.0 μm using, for example, a parylene which serves as a biocompatible coating on the first insulating layer 32. Note that use of a parylene containing fluorine as the parylene forming the exterior protection film 33 makes it possible to increase resistance to stains including protein and allows the ultrasonic endoscope 1 according to the present embodiment to more reliably perform the work of cleaning, disinfecting, and sterilizing the ultrasonic transducer portion 20. The exterior protection film 33 is, of course, not limited to a parylene film and may be, for example, a silicon nitride (SiN) film or polyimide (PI) film.

As shown in FIG. 8, a part of the flexible sheet 39 extending from a proximal end of the transducer elements 25 serves as the cable connection board portion 24 described above. Signal electrode pads 24a, insulating portions 24b, and return (ground) electrode pads 24c are printed at a surface of the cable connection board portion 24. Each signal electrode pad 24a is electrically connected to an inner lead 27a of a coaxial cable 27 with solder or the like. Each return (ground) electrode pad 24c is electrically connected to an outer lead (mesh-textured wire) 27b of the coaxial cable 27 with solder or the like. The pads 24a and 24c are printed at the surface of the cable connection board portion 24 of the flexible sheet 39 by gold and nickel (Au/Ni) plating.

Note that although not shown, the signal electrode pad 24a is electrically connected to the lower electrode 35 within the corresponding transducer element 25, and the ground electrode pad 24c is electrically connected to the upper electrode 31 within the corresponding transducer element 25.

A method for manufacturing the transducer portion 20 having the transducer elements 25 formed therein, in each of which the cells 30 with the above-described configuration according to the present embodiment are arrayed, will be described on the basis of FIGS. 9 to 20 and steps (S1 to S15) in a flow chart in FIG. 21. Note that although FIGS. 9 to 20 each show a section of the two c-MUT cells 30 to be formed, steps in forming the plurality of transducer elements 25 including the plurality of fine diaphragmatic c-MUT cells 30 by a silicon micromachining technique will be described in a following explanation. Note that the number of c-MUT cells 30 within one transducer element 25 is not limited to two or more and may be one.

A thick oxide film-coated wafer 45 which is a low-resistivity silicon (Si) substrate having the oxide film (a thermal oxide film of silicon dioxide ($SiO_2$) with a thickness of 1.5 μm which is to constitute a second insulating layer later) 32 and an oxide film 32a formed on two surfaces of a base silicon (Si) portion 43 with a thickness of 525 μm is prepared as a first substrate (S1), as shown in FIG. 9. A film of platinum (Pt) is first formed (to a thickness of 0.4 μm in the present embodiment) by sputtering, is patterned by photolithography, and is etched. Thereby, the upper electrodes 31 serving as first electrodes are formed, as shown in FIG. 10 (S2). At this time, the patterning is performed such that the adjacent upper electrodes 31 are electrically connected via the conducting portion 31a formed integrally with the upper electrodes 31, as shown in FIG. 7.

A silicon oxide ($SiO_2$) film with a thickness of 0.15 μm is formed at the thick oxide film-coated wafer 45 having the upper electrodes 31, thereby forming the second insulating layer 34 on the upper electrode 31 (on an upper surface side in FIG. 11) (S3). Note that the silicon oxide film may be formed on all surfaces of the thick oxide film-coated wafer 45 or only one of the surfaces where the upper electrodes 31 are formed.

With the steps in steps S1 to S3 described above, the first substrate, in which the upper electrodes 31 and second insulating layer 34 are formed on the thick oxide film-coated wafer 45, is fabricated.

As shown in FIG. 12, an SOI (Silicon on Insulator) wafer 47 is prepared next as a second substrate (S4). In the SOI wafer 47 according to the present invention, the third insulating layer 36, which is a BOX (Buried Oxide) made of a thermal silicon oxide ($SiO_2$) film with a thickness of 0.3 μm, is formed on a surface of a base silicon (Si) portion 46, and the lower electrode 35 with a thickness of 2.0 μm, which is made of low-resistivity silicon (Si), is formed on the third insulating layer 36.

The SOI wafer 47 is further thermally oxidized, thereby forming thermal silicon oxide ($SiO_2$) films 48 with a thickness of 0.4 μm, as shown in FIG. 13 (S5). The thermal silicon oxide film 48 on the lower electrode 35 side is coated with a resist and is etched by photolithography using BHF (a hydrofluoric acid buffer solution) to form outer shapes of the cavities 51 (S6).

With the step in step S6, a part of the thermal silicon oxide film 48 which is left after etching and patterning serves as the partition portion 41 forming outer peripheral surfaces of the cavities 51, as shown in FIG. 14.

With the steps in steps S4 to S6 described above, the second substrate, in which the partition portion 41 is formed on a surface of the SOI wafer 47 (a surface on the upper electrodes 31 side), is fabricated.

Surfaces of the second insulating layer 34 and partition portion 41, which are respectively formed on the wafers 45 and 47 and are silicon oxide films, are activated (S7). At this time, the surface activation step is performed using, e.g., $O_2$ plasma in the present embodiment. Note that UV irradiation, ionized gas, argon (Ar) plasma, or the like may be used for the activation of the silicon oxide films, instead of $O_2$ plasma.

As shown in FIG. 15, bonding surfaces which are the activated surfaces of the second insulating layer 34 and partition portion 41 are bonded while the wafers 45 and 47 are arranged at predetermined positions such that the cavities 51 are interposed between the upper electrodes 31 and the lower electrode 35 (S8).

As shown in FIG. 16, the base silicon portion 46 of the SOI wafer 47 no longer required is etched and removed using KOH (a potassium hydroxide solution) and BHF (a hydrofluoric acid buffer solution), together with the thermal silicon oxide film ($SiO_2$ film) 48 (S9).

As shown in FIG. 17, the inner protection film 37 is formed to a thickness of 1.0 μm on the third insulating layer 36. As a method for forming the inner protection film 37, a method for forming an insulating film such as a silicon nitride (SiN) film (a silicon dioxide ($SiO_2$) film, a parylene film, or the like may be substituted) by vapor deposition such as PVD (physical vapor deposition) or CVD (chemical vapor deposition) can be adopted (S10).

As shown in FIG. 18, polyimide (PI) is spin-coated on the inner protection film 37 and is baked (subjected to thermal processing), thereby forming the flexible sheet 39 with a thickness of 20.0 μm (S11). As shown in FIG. 19, the base silicon portion 43 of the thick oxide film-coated wafer 45 is etched and removed using KOH (a potassium hydroxide solution) and BHF (a hydrofluoric acid buffer solution), together with the thermal silicon oxide ($SiO_2$) film 32a (S12). Note that the cross-sectional views in FIG. 19 and subsequent drawings are opposite in vertical orientation to the cross-sectional views in FIGS. 10 to 18.

After that, to form the transducer elements 25, the inter-cell-group etching groove 28 is formed at a position where the partition portion 41 is formed by dry etching to reach the flexible sheet 39, as shown in FIG. 20 (S13). With this operation, the transducer elements 25 as segments are formed on the flexible sheet 39, and the transducer elements 25 can be deformed along the inter-cell-group etching groove 28. More specifically, since the flexible sheet 39 has low rigidity and is deformable, the flexible sheet 39 is bendable along the transducer elements 25.

As shown in FIGS. 6 and 8, the transducer elements 25 of the transducer portion 20 are bent into a predetermined bending state, to suit a shape of the ultrasonic transducer portion 20 of the ultrasonic endoscope 1 which is a cylindrical shape in the present embodiment (S14). In this state, the exterior protection film 33 with a thickness of 1.0 μm is finally formed by vapor deposition (e.g., CVD or PVD) using a parylene.

With the series of steps described above, the transducer elements 25 constituting an ultrasonic transducer, which have the c-MUT cells 30 formed therein, are manufactured. Note that lastly the pads 24a and 24c of the cable connection board portion 24 and the conductors 27a and 27b of the coaxial cable 27 are soldered.

As described above, since the ultrasonic transducer according to the present embodiment has a configuration in which the c-MUT cells 30 are formed on the flexible sheet 39, so-called crosstalk caused by interference between vibrations can be reduced compared to a conventional transducer element formed on a rigid substrate. For this reason, undesired vibrations in each transducer element 25 decrease, and a high-resolution image is obtained.

Since the c-MUT cells 30 are formed on the flexible sheet 39, the ultrasonic transducer is also advantageous in that undesired vibrations can be absorbed by the flexible sheet 39. The flexible sheet 39 can be easily deformed along the inter-cell-group etching grooves 28 at edges of each transducer element 25, and thus, flexibility in the shape of the ultrasonic transducer portion 20 increases. As a result, especially in the ultrasonic endoscope 1 to be inserted into a body, a size and thickness of the ultrasonic transducer portion 20 can be reduced, and the ultrasonic endoscope 1 becomes excellent in an ability to reduce pain of a patient, an ability to reduce invasiveness, and the like. Note that the flexible sheet (substrate) 39 of polyimide or the like can be formed to be thinner than a conventional rigid substrate, thus leading to a reduction in size of the transducer elements 25.

Note that as for a size reduction, a three-layer rigid body portion composed of the lower electrode 35 with the thickness of 2.0 µm, the third insulating layer 36 with the thickness of 0.3 µm, and the inner protection film 37 with the thickness of 1.0 µm, which is much thinner than the flexible sheet 39 with the thickness of 20.0 µm, is formed in the present embodiment.

As for the three-layer rigid body portion, setting of the thicknesses of the layers and selection of materials for forming the layers are performed such that rigidity of the three-layer rigid body portion is higher than that of the membrane 38. For this reason, a shake of the membrane 38 side with low rigidity makes it possible to efficiently generate ultrasonic vibrations from a surface of the exterior protection film 33. Note that the rigid body portion is formed by using a combination of a thin-film conductive material and a thin-film rigid insulator or dielectric as materials for the lower electrode 35, third insulating layer 36, and inner protection film 37.

In the transducer elements 25 according to the present embodiment, to bond the second insulating layer 34 and partition portion 41 forming the cavity 51 between the pair of electrodes of each c-MUT cell 30, a same material (a silicon oxide ($SiO_2$) film) is used for both the second insulating layer 34 and the partition portion 41. Since surface activation places atoms at the bonding surfaces into an active state apt to form a chemical bond, bonding strength of a bonding interface portion between the bonding surfaces can be increased.

Consequently, with the above-described manufacturing method, the transducer elements 25 are configured to be completely capable of preventing peeling at the bonding interface portions between the second insulating layers 34 and the partition portions 41, especially in a manufacturing process in which high heat is applied by CVD or the like. Since the second insulating layers 34 and partition portions 41 are tightly bonded, high heat at the time of high-pressure steam sterilization in reprocessing becomes less likely to cause peeling at the bonding interface portions between the second insulating layers 34 and the partition portions 41 in the ultrasonic endoscope 1 according to the present embodiment.

Activation of the bonding surfaces allows bonding at a low temperature. If flatness of each of the bonding surfaces of the second insulating layers 34 and partition portions 41 is improved, room-temperature bonding becomes possible. If low-temperature bonding becomes possible, the number of choices for a conductive material which can be used for the lower electrodes 35 increases, and thus, a cost reduction can be achieved.

In the present embodiment, the thick oxide film-coated wafer 45, which is a low-resistivity silicon substrate with a resistivity as low as 0.5 Ω·cm or less, is used as a base substrate for forming the c-MUT cells 30. This is because the low-resistivity silicon substrate itself can be used as a wiring route. However, since use of a high-resistivity substrate is preferable in order to reduce a parasitic capacitance to a minimum, the base substrate need not be limited to a low-resistivity silicon substrate, but a high-resistivity substrate may be used instead. Whichever substrate is used, oxide film formation can be similarly performed. Since the manufacturing method makes it possible to tightly bond the second insulating layers 34 and partition portions 41, the transducer elements 25 with high bonding strength can be fabricated irrespective of which configuration is adopted.

(Second Embodiment)

A second embodiment of the present invention will be described next with reference to FIGS. 22 to 35. Note that the present embodiment is an example in which c-MUT cells 30 are formed on a flexible sheet 39 by a surface technique, thereby forming a plurality of transducer elements 25. For this reason, in a following explanation, same components as those in the first embodiment are denoted by same reference numerals, a description thereof will be omitted, and only differences will be described.

Figure 22:
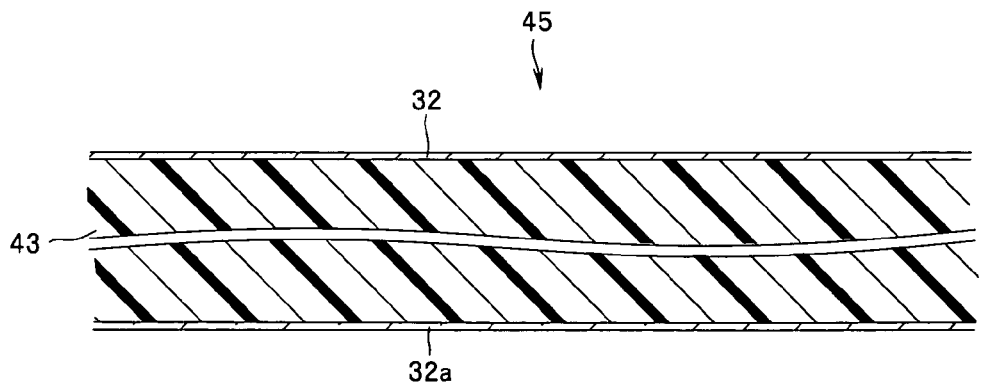
FIG. 22 is a cross-sectional view showing a thick oxide film-coated wafer according to a second embodiment.
Figure 23:
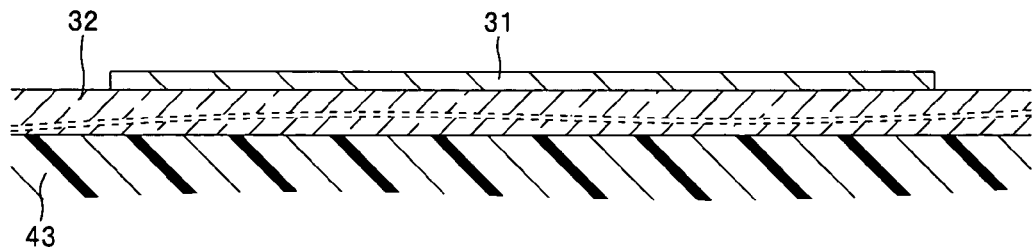
FIG. 23 is a cross-sectional view showing a part of a process of manufacturing a c-MUT cell in a state in which an upper electrode is formed on the thick oxide film-coated wafer in the second embodiment.
Figure 24:
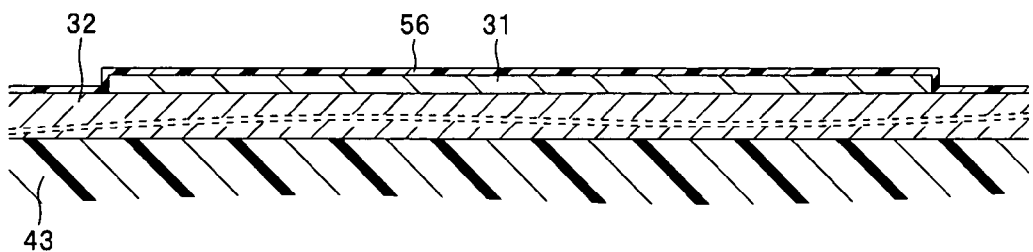
FIG. 24 is a cross-sectional view showing a part of the process of manufacturing a c-MUT cell in a state in which an insulating layer is formed in the second embodiment.
Figure 25:
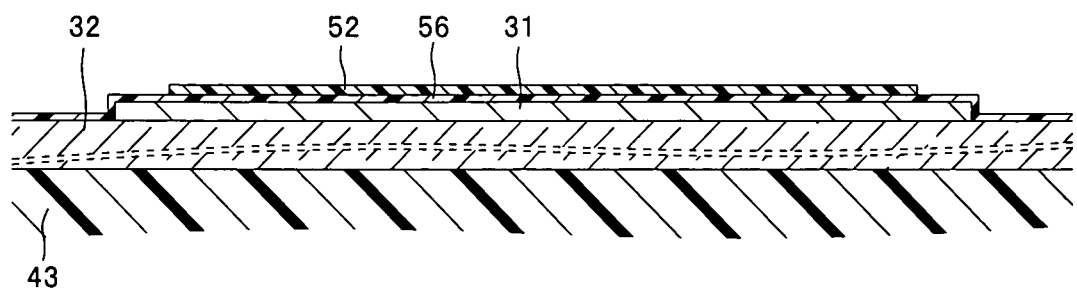
FIG. 25 is a cross-sectional view showing a part of the process of manufacturing a c-MUT cell in a state in which a sacrificial layer is formed in the second embodiment.
Figure 26:
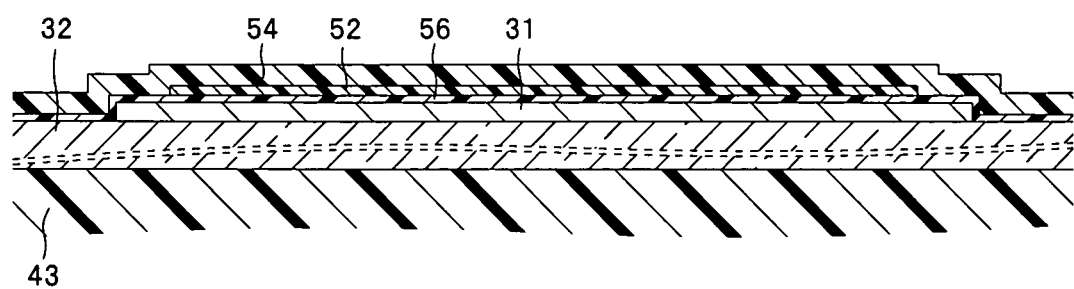
FIG. 26 is a cross-sectional view showing a part of the process of manufacturing a c-MUT cell in a state in which an insulating layer is formed in the second embodiment.
Figure 27:
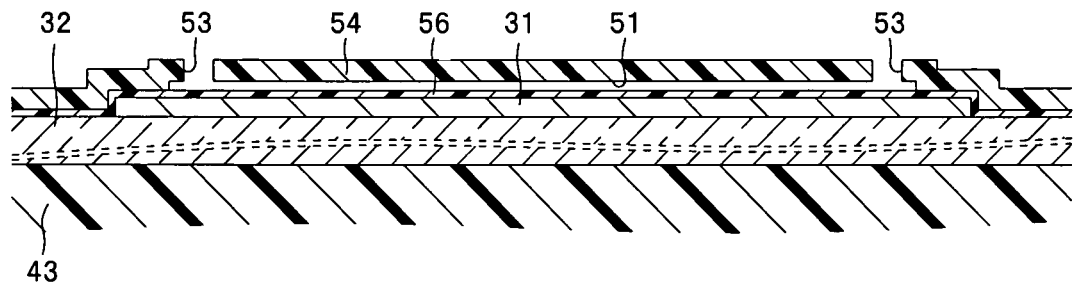
FIG. 27 is a cross-sectional view showing a part of the process of manufacturing a c-MUT cell in a state in which sacrificial layer removing holes are formed, and the sacrificial layer is removed in the second embodiment.
Figure 28:
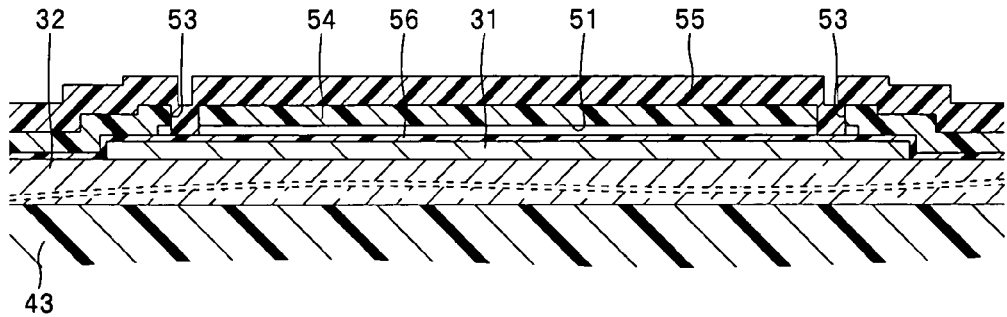
FIG. 28 is a cross-sectional view showing a part of the process of manufacturing a c-MUT cell in a state in which an insulating layer which seals the sacrificial layer removing holes is formed in the second embodiment.
Figure 29:
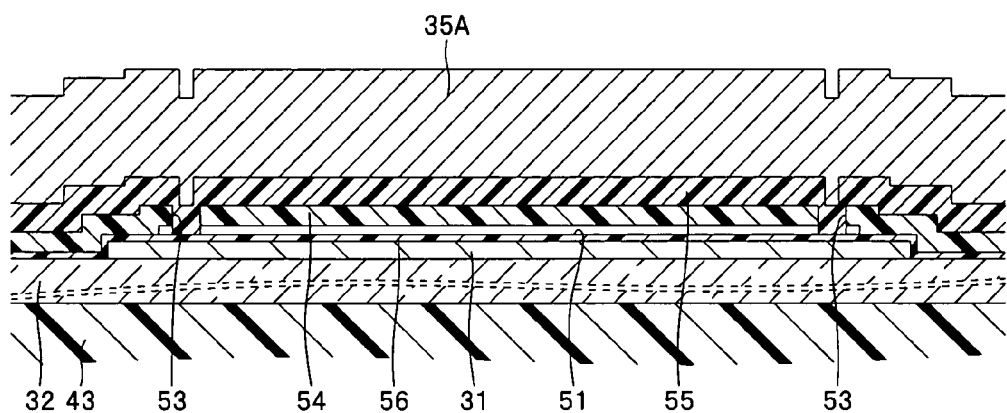
FIG. 29 is a cross-sectional view showing a part of the process of manufacturing a c-MUT cell in a state in which a conductive film is formed in the second embodiment.
Figure 30:
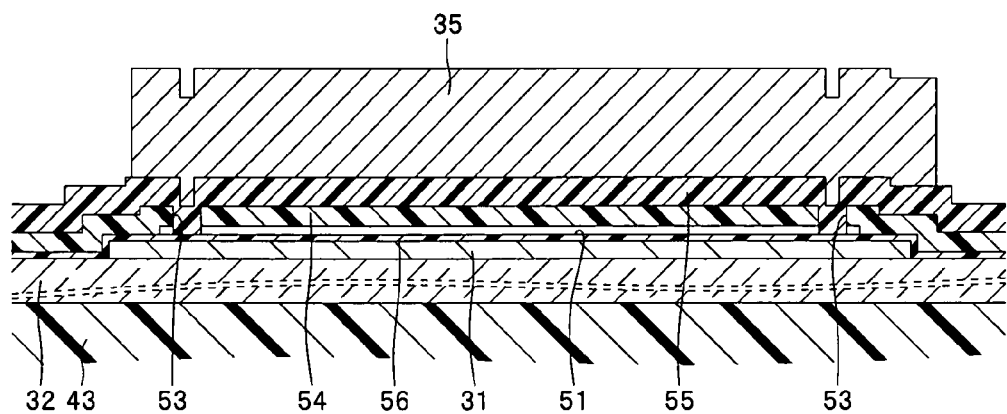
FIG. 30 is a cross-sectional view showing a part of the process of manufacturing a c-MUT cell in a state in which a lower electrode is formed by etching in the second embodiment.
Figure 31:
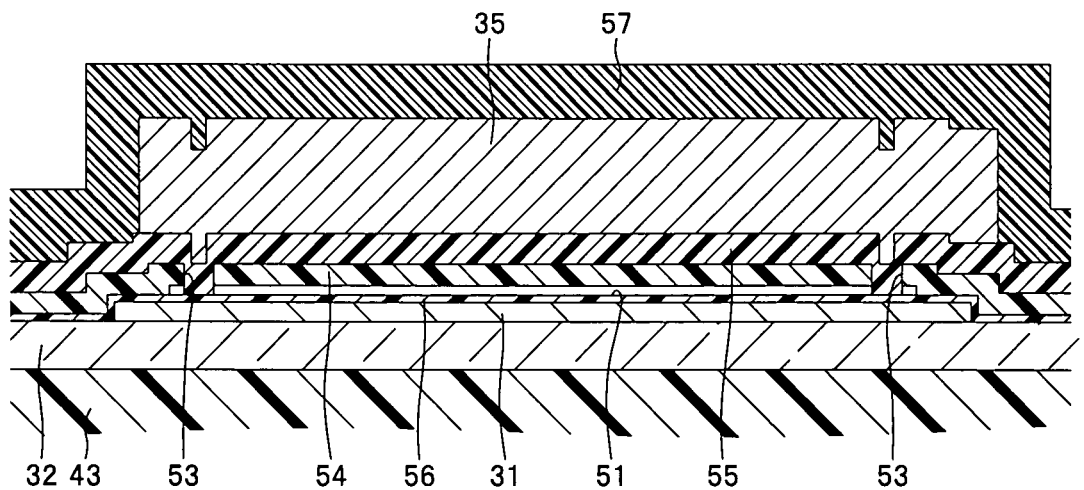
FIG. 31 is a cross-sectional view showing a part of the process of manufacturing a c-MUT cell in a state in which an inner protection film is formed in the second embodiment.
Figure 32:
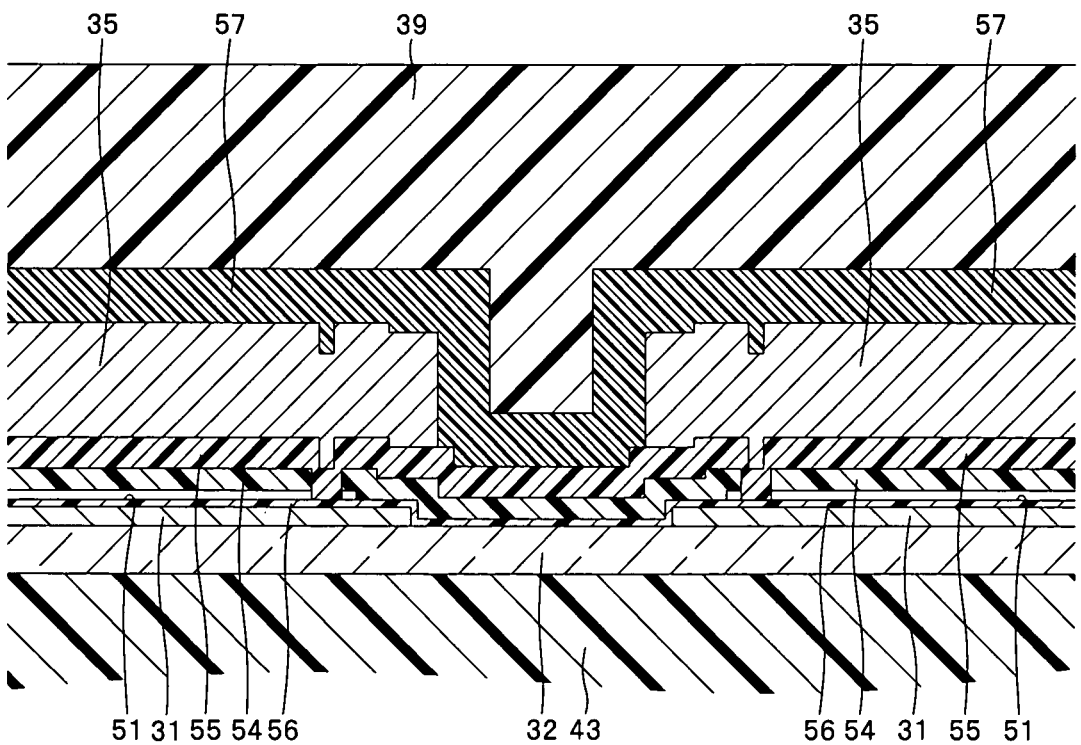
FIG. 32 is a cross-sectional view showing a part of the process of manufacturing a c-MUT cell in a state in which a flexible sheet is formed on the protection film in the second embodiment.
Figure 33:
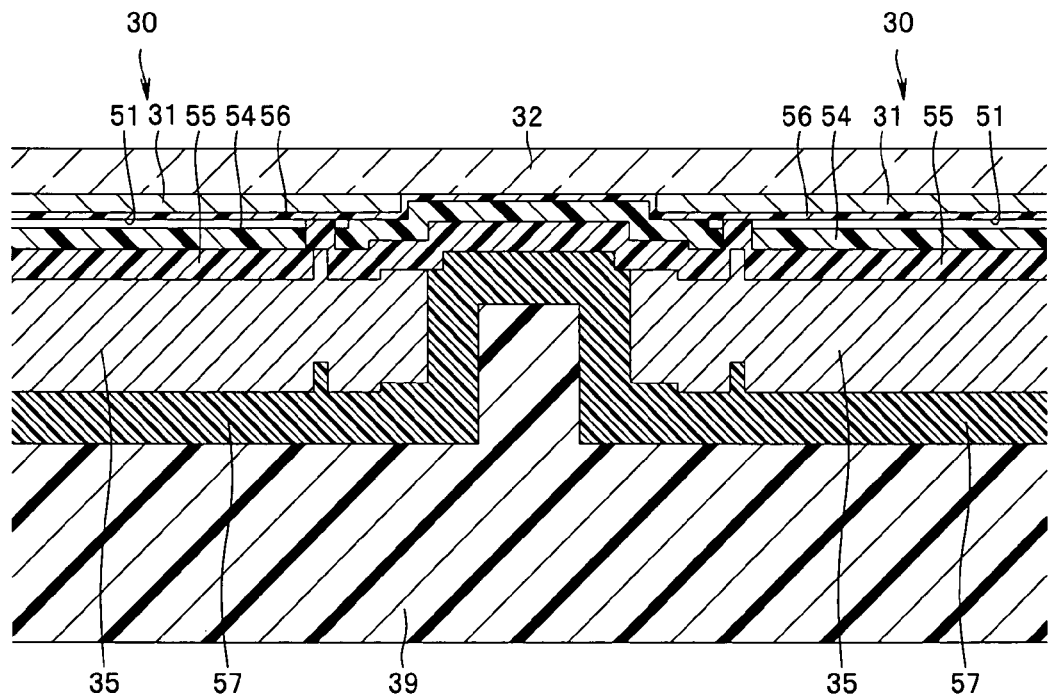
FIG. 33 is a cross-sectional view showing a part of the process of manufacturing a c-MUT cell in a state in which a base silicon portion of the thick oxide film-coated wafer is etched and removed in the second embodiment.
Figure 34:
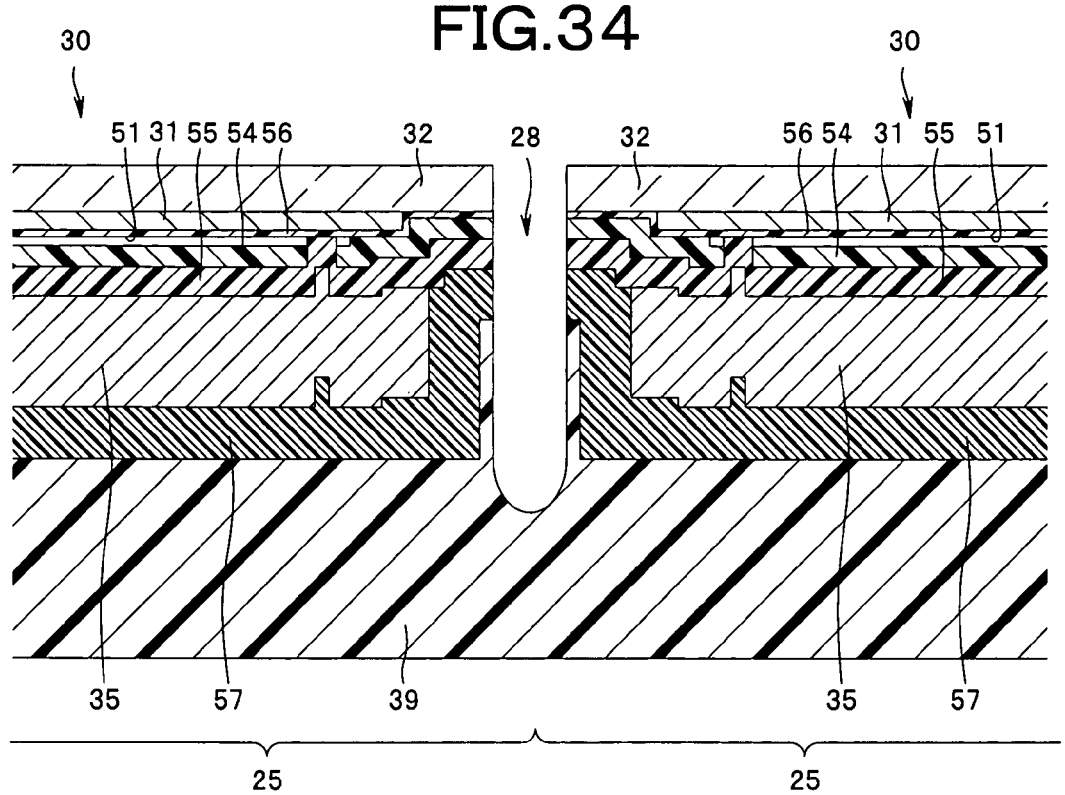
FIG. 34 is a cross-sectional view showing a part of the process of manufacturing a c-MUT cell in a state in which an inter-cell-group etching groove is formed in the second embodiment.
Figure 35:
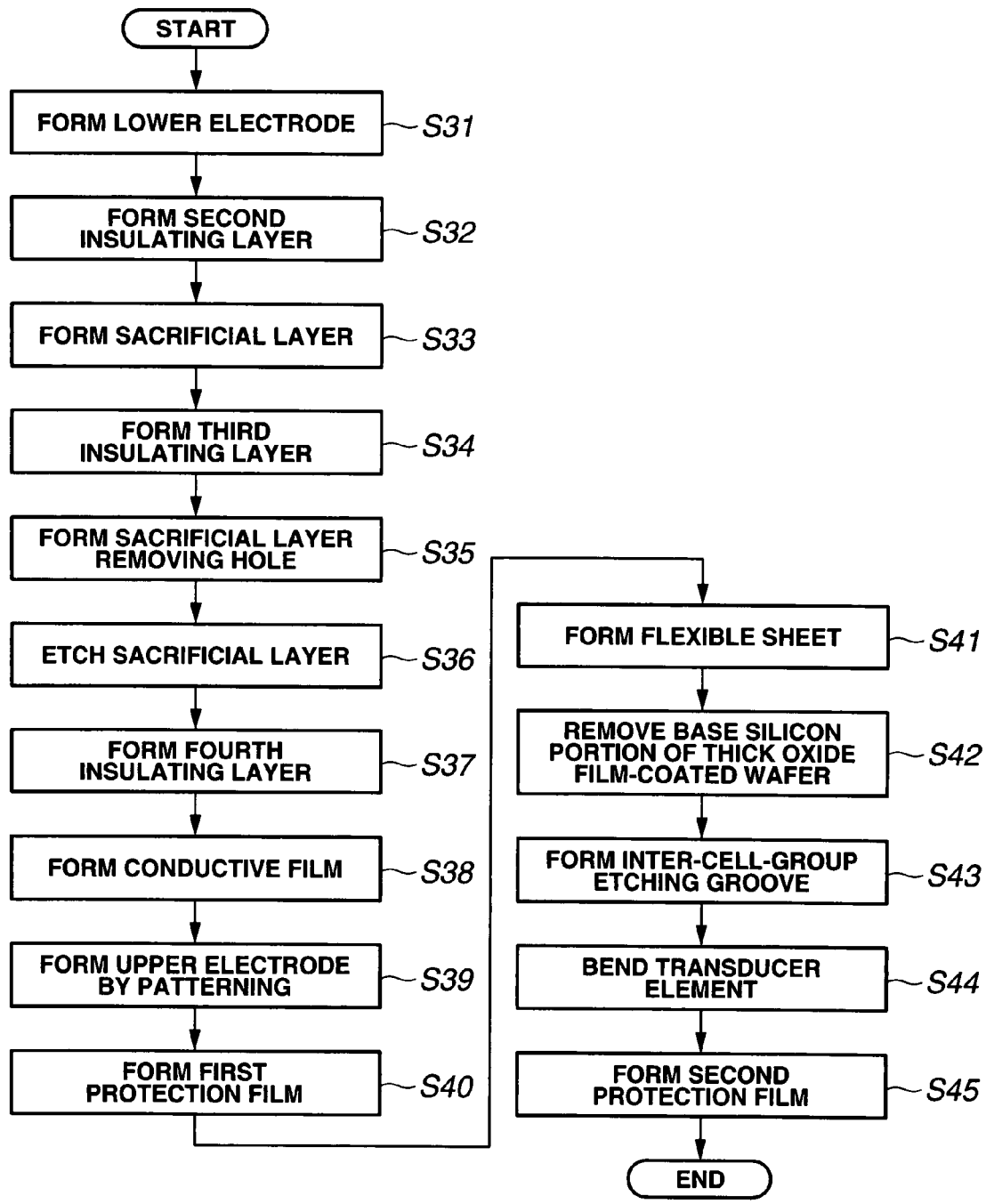
FIG. 35 is a flow chart showing steps in manufacturing a c-MUT cell in the second embodiment.

FIGS. 22 to 35 show the second embodiment. FIG. 22 is a cross-sectional view showing a thick oxide film-coated wafer. FIG. 23 is a cross-sectional view showing a part of a process of manufacturing a c-MUT cell in a state in which an upper electrode is formed on the thick oxide film-coated wafer. FIG. 24 is a cross-sectional view showing a part of the process of manufacturing a c-MUT cell in a state in which an insulating layer is formed. FIG. 25 is a cross-sectional view showing a part of the process of manufacturing a c-MUT cell in a state in which a sacrificial layer is formed. FIG. 26 is a cross-sectional view showing a part of the process of manufacturing a c-MUT cell in a state in which an insulating layer is formed. FIG. 27 is a cross-sectional view showing a part of the process of manufacturing a c-MUT cell in a state in which sacrificial layer removing holes are formed, and the sacrificial layer is removed. FIG. 28 is a cross-sectional view showing a part of the process of manufacturing a c-MUT cell in a state in which an insulating layer which seals the sacrificial layer removing holes is formed. FIG. 29 is a cross-sectional view showing a part of the process of manufacturing a c-MUT cell in a state in which a conductive film is formed. FIG. 30 is a cross-sectional view showing a part of the process of manufacturing a c-MUT cell in a state in which a lower electrode is formed by etching. FIG. 31 is a cross-sectional view showing a part of the process of manufacturing a c-MUT cell in a state in which an inner protection film is formed. FIG. 32 is a cross-sectional view showing a part of the process of manufacturing a c-MUT cell in a state in which a flexible sheet is formed on the protection film. FIG. 33 is a cross-sectional view showing a part of the process of manufacturing a c-MUT cell in a state in which a base silicon portion of the thick oxide film-coated wafer is etched and removed. FIG. 34 is a cross-sectional view showing a part of the process of manufacturing a c-MUT cell in a state in which an inter-cell-group etching groove is formed. FIG. 35 is a flow chart showing steps in manufacturing a c-MUT cell.

A method for manufacturing the transducer elements 25 according to the present embodiment will be described on the basis of FIGS. 22 to 34 and steps (S31 to S45) in a flow chart in FIG. 35. Note that although FIGS. 22 to 34 each show a section of one or two c-MUT cells 30 to be formed, steps in forming the plurality of transducer elements 25 including the plurality of fine diaphragmatic c-MUT cells 30 on one thick oxide film-coated wafer 45 by a silicon micromachining technique will be described in a following explanation in a same manner as in the first embodiment.

As shown in FIG. 22, first, the thick oxide film-coated wafer 45, in which first insulating layers 32 and 32a which are silicon oxide ($SiO_2$) films with a thickness of 10 μm or thereabout are formed on both surfaces of a base silicon portion 43, is prepared, and a film of molybdenum (Mo) with a thickness of 0.4 μm is formed on a surface of the thick oxide film-coated wafer 45 by sputtering. As shown in FIG. 23, the formed molybdenum (Mo) film is patterned by photolithography to form an upper electrode 31 (S31).

A film of silicon nitride (SiN) with a thickness of 0.15 μm is formed by CVD (chemical vapor deposition) on the surface of the thick oxide film-coated wafer 45 having the upper electrode 31, as shown in FIG. 23, thereby forming a second insulating layer 56, as shown in FIG. 24 (S32).

A film of phosphorus doped low-temperature silicon dioxide (PSG) with a thickness of 0.2 μm is formed on the second insulating layer 56 by CVD and is patterned by photolithography to form a sacrificial layer 52, as shown in FIG. 25 (S33). The patterning determines a dimension of a cavity 51 described above. Note that there are available various choices, such as silicon dioxide ($SiO_2$), silicon nitride (SiN), polysilicon, and a metal, for a material for the sacrificial layer in a surface micromachining process. The material for the sacrificial layer is not limited to phosphorus doped low-temperature silicon dioxide (PSG) in the present embodiment.

A film of silicon nitride (SiN) with a thickness of 0.45 μm is formed on an upper surface of the second insulating layer 56 having the sacrificial layer 52 by CVD, thereby forming a third insulating layer 54, as shown in FIG. 26 (S34). Sacrificial layer removing holes 53 for introducing a chemical solution for removing the sacrificial layer 52 are formed at predetermined positions of the third insulating layer 54 on the sacrificial layer 52 by dry etching (S35).

The sacrificial layer 52 is etched and removed through the formed sacrificial layer removing holes 53 using a chemical solution containing HF (hydrofluoric acid) (S36). With this operation, the sacrificial layer 52 is gradually removed by the chemical solution, and an air gap is formed between the second insulating layer 56 and the third insulating layer 54. The cavity 51 and a channel which serves as a passage when the sacrificial layer 52 dissolves and is etched through the sacrificial layer removing holes 53 are formed, as shown in FIG. 27. The channel is opened by the sacrificial layer removing holes 53.

Note that since the sacrificial layer 52 is made of phosphorus doped low-temperature silicon dioxide (PSG), the second insulating layer 56 and third insulating layer 54 are hardly etched, and only the sacrificial layer 52 can be etched and removed using the chemical solution containing hydrofluoric acid (HF). For this reason, it is possible to form the cavities 51 of the cells 30 in a uniform shape.

As shown in FIG. 28, a fourth insulating layer 55 which is a silicon dioxide ($SiO_2$) film with a thickness of 0.4 μm is formed on an upper surface of the third insulating layer 54 by sputtering (S37). At this time, the fourth insulating layer 55 is deposited to fill the sacrificial layer removing holes 53. Note that a material used in step S37 is not limited to silicon dioxide ($SiO_2$), and an insulating material such as silicon nitride (SiN) may be used instead.

Since the fourth insulating layer 55, which is to fill the sacrificial layer removing holes 53 for etching the sacrificial layer 52, is formed by sputtering (vacuum evaporation may be substituted), the fourth insulating layer 55 can also be deposited immediately below the sacrificial layer removing holes 53. For this reason, sample particles constituting the fourth insulating layer 55 are not deposited in the cavity 51, and thus, it is possible to form the cavity 51 in a stable shape.

More specifically, since the fourth insulating layer 55 is not formed by CVD, and the fourth insulating layer 55 does not extend into the cavity 51 when being formed, it is possible to form the sacrificial layer removing holes 53 to be larger than conventional ones. This facilitates etching of the sacrificial layer 52 and makes it possible to increase a rate at which the sacrificial layer 52 is etched. Since the second insulating layer 56 and third insulating layer 54 are prevented from being unnecessarily etched, it is possible to form the cavity 51 in a stable shape.

A film of molybdenum (Mo) with a thickness of 1.0 μm is formed on an upper surface of the fourth insulating layer 55 by sputtering, thereby forming a conductive film 35A, as shown in FIG. 29 (S38). Note that a material for the conductive film 35A is not limited to molybdenum (Mo), and a conductive material such as platinum (Pt) may be used instead. Also note that conductive materials may be stacked or a conductive material and an insulating material may be combined as far as an electrode function is fulfilled, thereby increasing strength of the conductive film 35A.

As shown in FIG. 30, the conductive film 35A is patterned by photolithography to form a lower electrode 35 (S39). Note that although the conductive film 35A is formed by sputtering in the present embodiment, the present invention is not limited to the method, and the film may be formed by, for example, vacuum evaporation.

As shown in FIG. 31, an insulating film such as a silicon nitride (SiN) film (a silicon dioxide ($SiO_2$) film, a parylene film, or the like may be substituted) is formed to a thickness of 5.0 μm on the lower electrode 35 by deposition such as PVD (physical vapor deposition) or CVD (chemical vapor deposition), thereby forming an inner protection film 57 serving as a first protection film (S40).

As shown in FIG. 32, polyimide (PI) is spin-coated on the inner protection film 57 and is baked (subjected to thermal processing), thereby forming the flexible sheet 39 with a thickness of 20.0 μm (S41). As shown in FIG. 33, the base silicon portion 43 of the thick oxide film-coated wafer 45 is etched and removed using KOH (a potassium hydroxide solution) and BHF (a hydrofluoric acid buffer solution), together with the thermal silicon oxide ($SiO_2$) film 32a (S42). Note that the cross-sectional views in FIG. 33 and subsequent drawings are opposite in vertical orientation to the cross-sectional views in FIGS. 22 to 32.

After that, to form the transducer elements 25 as segments, an inter-cell-group etching groove 28 is formed at a predetermined position between the cells 30 by dry etching to reach the flexible sheet 39, as shown in FIG. 34 (S43). With this operation, the transducer elements 25 as the segments are formed on the flexible sheet 39 as in the first embodiment, and the transducer elements 25 can be deformed along the inter-cell-group etching groove 28. More specifically, since the flexible sheet 39 has low rigidity and is deformable, the flexible sheet 39 is bendable along the transducer elements 25.

Although not shown, the transducer elements 25 are bent to be placed into a predetermined bending state, to suit a shape of an ultrasonic transducer portion 20 of an ultrasonic endoscope 1 which is a cylindrical shape in a same manner as in the first embodiment (S44). In this state, an exterior protection film with a thickness of 1.0 µm is formed is finally formed by vapor deposition (e.g., CVD or PVD) using a parylene (S45).

With the series of steps of the surface technique described above, the transducer elements 25 constituting an ultrasonic transducer, which have the c-MUT cells 30 formed therein, are manufactured. As described above, the ultrasonic transducer according to the present embodiment can reduce so-called crosstalk caused by interference between vibrations compared to a conventional transducer element. Accordingly, undesired vibrations in each transducer element 25 decrease, and a high-resolution image is obtained.

Undesired vibrations in the transducer elements 25 according to the present embodiment can also be absorbed by the flexible sheet 39. The flexible sheet 39 can be easily deformed along the inter-cell-group etching grooves 28 at edges of each transducer element 25. Accordingly, especially in the ultrasonic endoscope 1 to be inserted into a body, a size and thickness of the ultrasonic transducer portion 20 can be reduced, and the ultrasonic endoscope 1 becomes excellent in an ability to reduce pain of a patient, an ability to reduce invasiveness, and the like. Note that the flexible sheet (substrate) 39 of polyimide or the like can be formed to be thinner than a conventional rigid substrate, thus leading to a reduction in size of the transducer elements 25. Note that rigidity of each transducer element 25 is increased by making the lower electrode 35 and the inner protection film 57 on a lower side of the lower electrode 35 thicker than portions constituting a membrane. For this reason, only the membrane side deforms at the time of electrostatic actuation, ultrasounds can be efficiently transmitted, and strength enough for bending is ensured.

A structure of and manufacturing steps for a capacitive ultrasonic transducer has been described in the present embodiment. It is easy to divert the present embodiment to manufacture of a piezoelectric micromachined ultrasonic transducer (p-MUT) by forming an electrode and a piezoelectric body after the formation of the third insulating layer 54 in step S34.

(Third Embodiment)

A third embodiment of the present invention will be described with reference to FIGS. 36 to 46. Note that the present embodiment is an example in which MUT elements are formed on a dielectric or insulating sheet by stacking thin films, thereby forming a plurality of transducer elements 25. Also in a following explanation, same components as those in the first and second embodiments are denoted by same reference numerals, a description thereof will be omitted, and only differences will be described.

Figure 36:
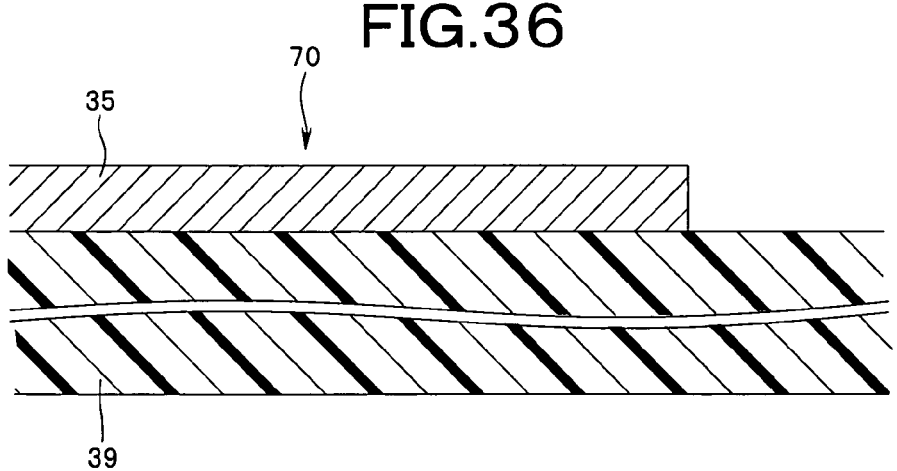
FIG. 36 is a cross-sectional view showing a flexible printed circuit board having a printed lower electrode according to a third embodiment.
Figure 37:
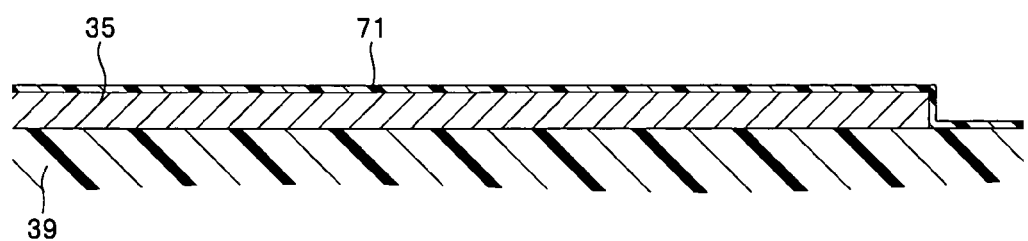
FIG. 37 is a cross-sectional view showing a part of a process of manufacturing a c-MUT cell in a state in which a first insulating layer is formed on the lower electrode in the third embodiment.
Figure 38:
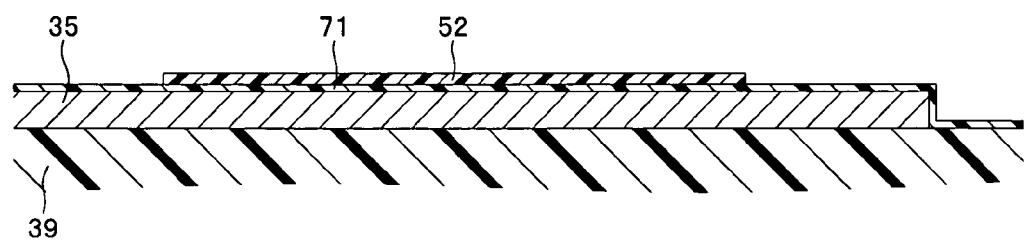
FIG. 38 is a cross-sectional view showing a part of the process of manufacturing a c-MUT cell in a state in which a sacrificial layer is formed in the third embodiment.
Figure 39:
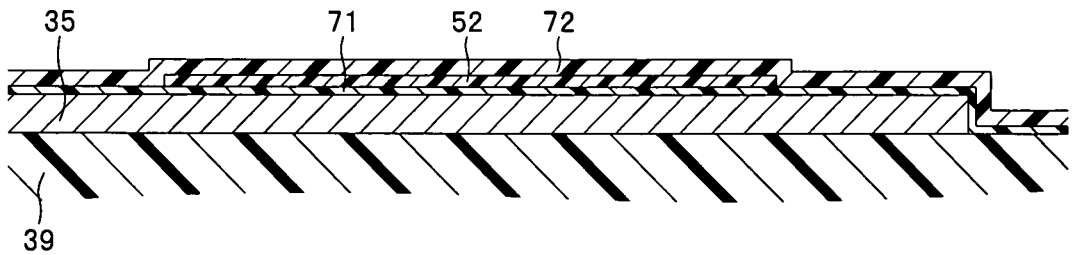
FIG. 39 is a cross-sectional view showing a part of the process of manufacturing a c-MUT cell in a state in which a second insulating layer is formed in the third embodiment.
Figure 40:
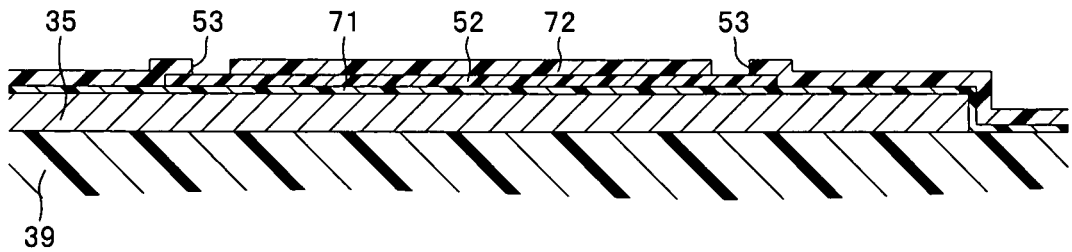
FIG. 40 is a cross-sectional view showing a part of the process of manufacturing a c-MUT cell in a state in which sacrificial removing holes are formed in the third embodiment.
Figure 41:
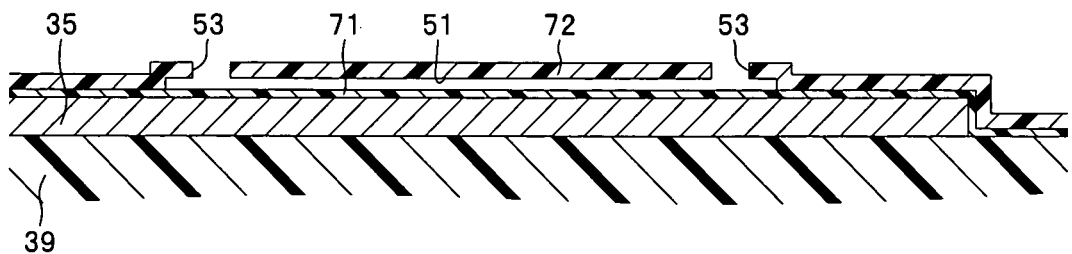
FIG. 41 is a cross-sectional view showing a part of the process of manufacturing a c-MUT cell in a state in which the sacrificial layer is etched, and a cavity is formed in the third embodiment.
Figure 42:
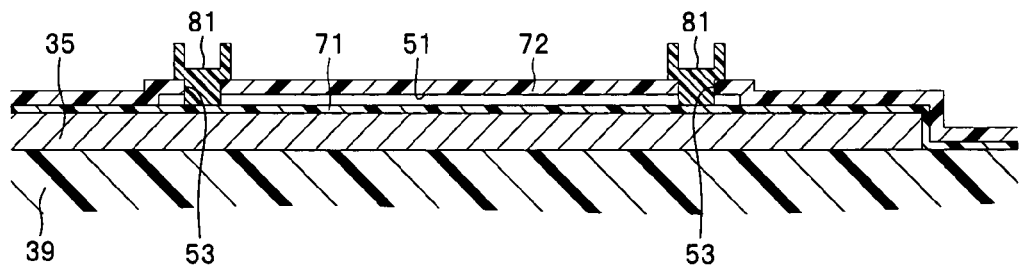
FIG. 42 is a cross-sectional view showing a part of the process of manufacturing a c-MUT cell in a state in which plugs which seal the sacrificial layer removing holes are formed in the third embodiment.
Figure 43:
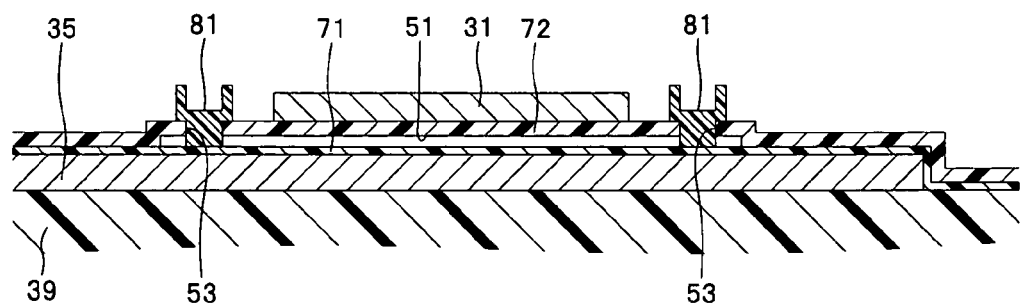
FIG. 43 is a cross-sectional view showing a part of the process of manufacturing a c-MUT cell in a state in which an upper electrode is formed in the third embodiment.
Figure 44:
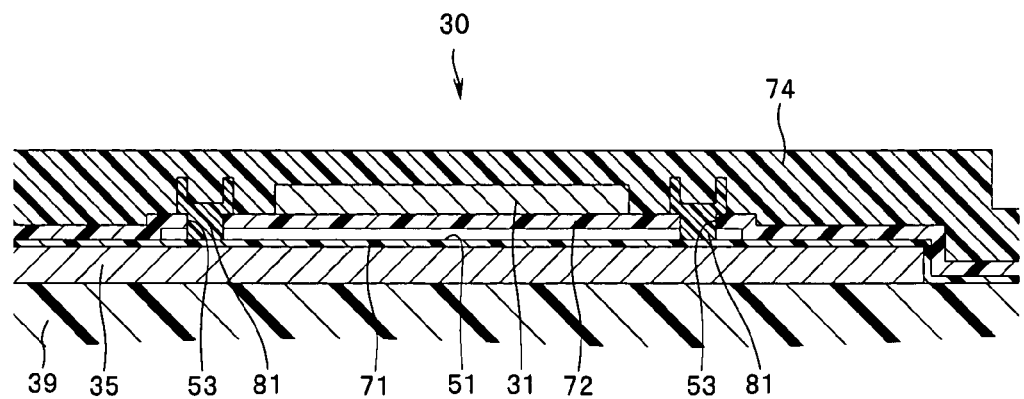
FIG. 44 is a cross-sectional view showing a part of the process of manufacturing a c-MUT cell in a state in which a third insulating layer is formed in the third embodiment.
Figure 45:
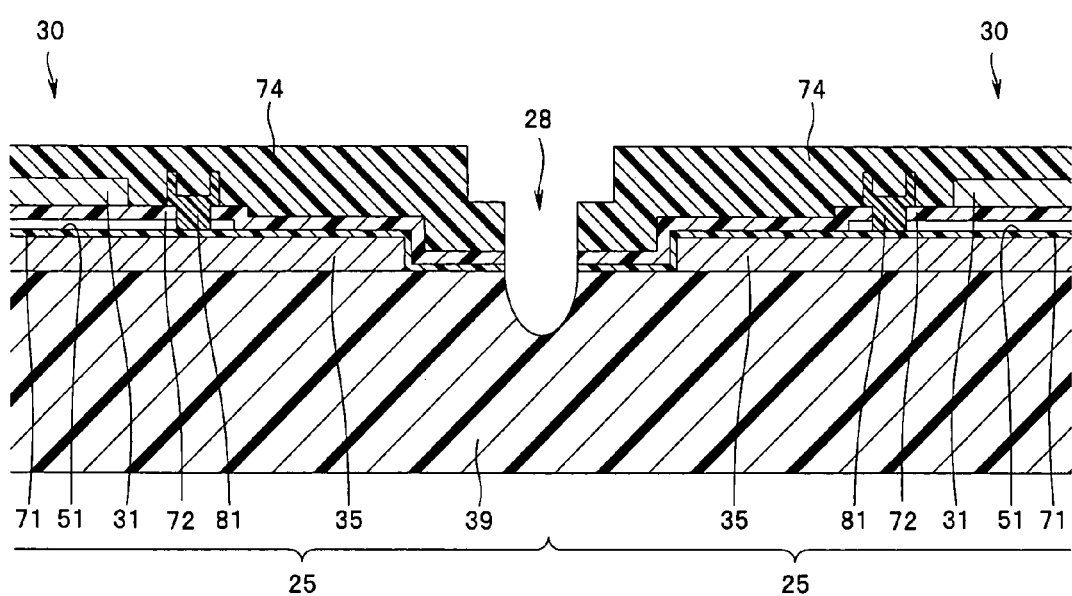
FIG. 45 is a cross-sectional view showing a part of the process of manufacturing a c-MUT cell in a state in which an inter-cell-group etching groove is formed in the third embodiment.
Figure 46:
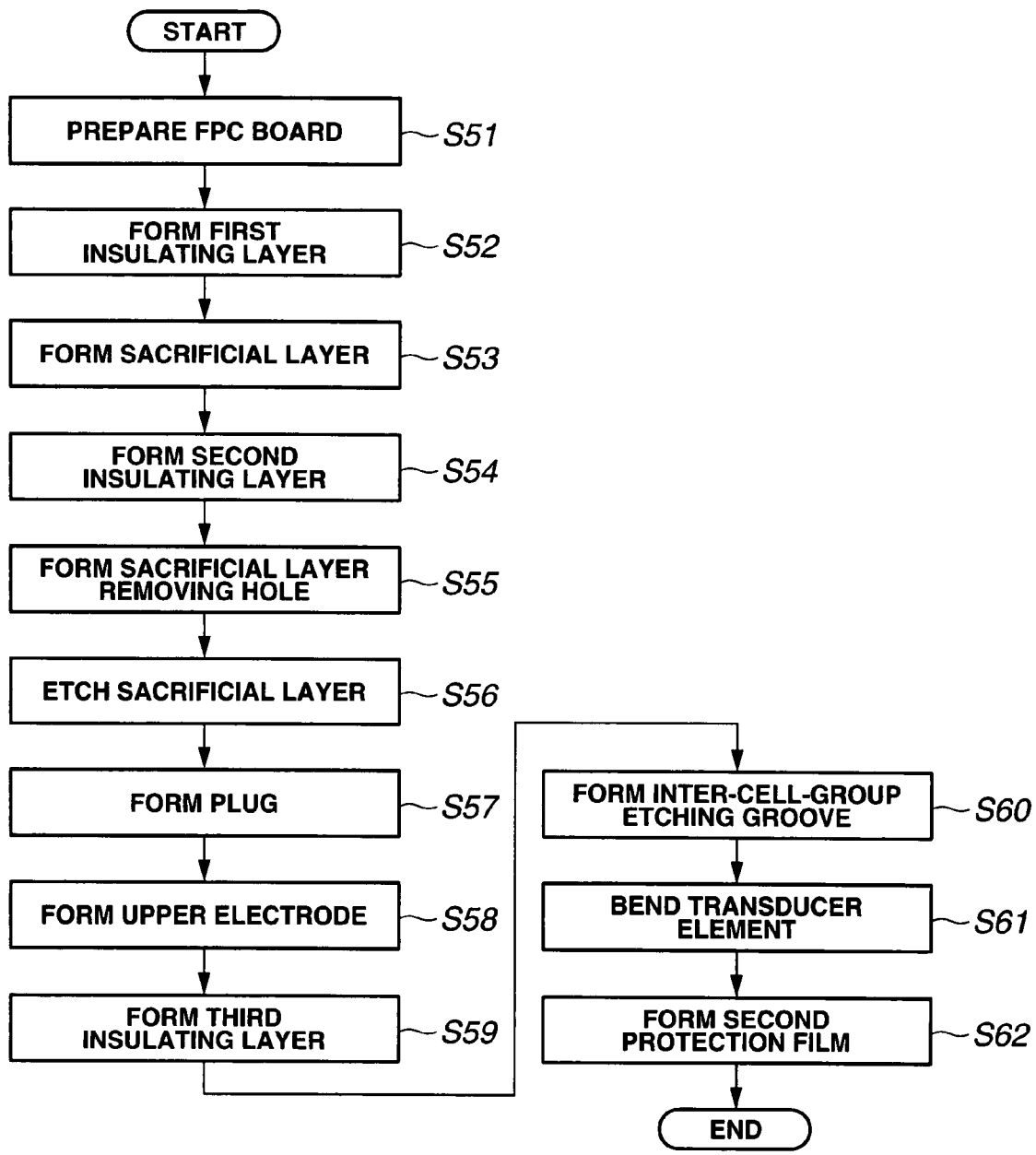
FIG. 46 is a flow chart showing steps in manufacturing a c-MUT cell in the third embodiment.

FIGS. 36 to 46 show the third embodiment. FIG. 36 is a cross-sectional view showing a flexible printed circuit board having a printed lower electrode. FIG. 37 is a cross-sectional view showing a part of a process of manufacturing a c-MUT cell in a state in which a first insulating layer is formed on the lower electrode. FIG. 38 is a cross-sectional view showing a part of the process of manufacturing a c-MUT cell in a state in which a sacrificial layer is formed. FIG. 39 is a cross-sectional view showing a part of the process of manufacturing a c-MUT cell in a state in which a second insulating layer is formed. FIG. 40 is a cross-sectional view showing a part of the process of manufacturing a c-MUT cell in a state in which sacrificial layer removing holes are formed. FIG. 41 is a cross-sectional view showing a part of the process of manufacturing a c-MUT cell in a state in which the sacrificial layer is etched, and a cavity is formed. FIG. 42 is a cross-sectional view showing a part of the process of manufacturing a c-MUT cell in a state in which plugs which seal the sacrificial layer removing holes are formed. FIG. 43 is a cross-sectional view showing a part of the process of manufacturing a c-MUT cell in a state in which an upper electrode is formed. FIG. 44 is a cross-sectional view showing a part of the process of manufacturing a c-MUT cell in a state in which a third insulating layer is formed. FIG. 45 is a cross-sectional view showing a part of the process of manufacturing a c-MUT cell in a state in which an inter-cell-group etching groove is formed. FIG. 46 is a flow chart showing steps in manufacturing a c-MUT cell.

A method for manufacturing the transducer elements 25 according to the present embodiment will be described on the basis of FIGS. 36 to 45 and steps (S51 to S62) in a flow chart in FIG. 46. Note that although FIGS. 36 to 45 each show a section of one or two c-MUT cells 30 to be formed, steps in forming the plurality of transducer elements 25 including one or more c-MUT cells 30 on a flexible substrate by a silicon micromachining technique will be described in a following explanation.

As shown in FIG. 36, first, a FPC (flexible printed circuit board) 70, on which a lower electrode 35 is printed, is prepared (S51). The FPC 70 according to the present embodiment is composed of a flexible sheet 39 with a thickness of, for example, 35 µm which is made of a flexible material such as polyimide (PI) and the lower electrode 35, which is a copper (Cu) foil with a gold (Au) film and is printed to a thickness of, for example, 18 µm on the flexible sheet 39. Note that a material for the flexible sheet 39 is not limited to polyimide, and any flexible material may be used as long as the flexible material is highly resistant to an etchant for a manufacturing process and can withstand a temperature during the manufacturing process. Also note that a material for the lower electrode 35 is not limited to a copper foil with a gold film, and any conductive foil material will do.

A first insulating layer 71 with a thickness of, for example, 0.15 µm which is made of an insulating material such as silicon dioxide ($SiO_2$) is formed by sputtering on a surface of the FPC 70 where the lower electrode 35 is formed (S52).

In a same manner as in the second embodiment, a film of phosphorus doped low-temperature silicon dioxide (PSG) with a thickness of 0.15 µm is formed on the first insulating layer 71 by CVD and is patterned by photolithography to form a sacrificial layer 52, as shown in FIG. 38 (S53). Note that polysilicon (poly-Si), which is used in a flat panel or the like and from which a film can be formed at a temperature as low as about 200° C., may be used for the sacrificial layer 52 instead of phosphorus doped low-temperature silicon dioxide. In this case, xenon difluoride ($XeF_2$) for dry etching can be used to remove the sacrificial layer 52.

A film of silicon dioxide ($SiO_2$) with a thickness of 0.2 µm is formed on an upper surface of the first insulating layer 71 having the sacrificial layer 52 by CVD, thereby forming a second insulating layer 72, as shown in FIG. 39 (S54). Like the second embodiment, sacrificial layer removing holes 53 for introducing a chemical solution or the like for removing the sacrificial layer 52 are formed at predetermined positions of the second insulating layer 72 on the sacrificial layer 52 by reactive ion etching (RIE) (S55).

The sacrificial layer 52 is etched through the formed sacrificial layer removing holes 53 using a chemical solution containing hydrofluoric acid (HF) (S56). With this operation, an air gap is formed between the first insulating layer 71 and the second insulating layer 72, thereby forming a cavity 51, as shown in FIG. 41.

A film of silicon dioxide ($SiO_2$) is formed on the second insulating layer 72 by sputtering and is etched by photolithography, thereby forming plugs 81 which seal the sacrificial layer removing holes 53 (S57). As described in the second embodiment, each plug 81 is deposited by sputtering such that the plug 81 follows an inner surface of the corresponding sacrificial layer removing hole 53. Accordingly, it is possible to seal the sacrificial layer removing holes 53 while keeping a shape of the cavity 51 stable.

A film of a conductive material such as molybdenum (Mo), tantalum (Ta), or platinum (Pt) is formed, by sputtering, at a position opposed to the lower electrode 35 on the second insulating layer 72 forming the cavity 51 and is etched by photolithography to have a predetermined shape (a circular surface shape in the present embodiment), thereby forming an upper electrode 31, as shown in FIG. 43 (S58).

After that, a film of silicon dioxide ($SiO_2$) is formed, thereby forming a third insulating layer 74, as shown in FIG. 44 (S59). Like the above-described embodiments, to form the transducer elements 25, an inter-cell-group etching groove 28 is formed at a predetermined position between the c-MUT cells 30, as shown in FIG. 45 (S60). With this operation, the transducer elements 25 as segments are formed on the flexible sheet 39 as in the above embodiments, and the transducer elements 25 can be deformed along the inter-cell-group etching groove 28. More specifically, since the flexible sheet 39 has low rigidity and is deformable, the flexible sheet 39 is bendable along the transducer elements 25.

Although not shown, the transducer elements 25 are bent to be placed into a predetermined bending state, to suit a shape of an ultrasonic transducer portion 20 of an ultrasonic endoscope 1 which is a cylindrical shape in a same manner as in the respective embodiments (S61). In this state, an exterior protection film with a thickness of 1.0 µm is finally formed by vapor deposition (e.g., CVD or PVD) using a parylene (S62).

As described above, the c-MUT cells 30 are formed on a dielectric or insulator sheet (the FPC 70 in the present embodiment) by stacking thin films. This makes it possible to form an ultrasonic transducer in which the plurality of transducer elements 25 separated by the inter-cell-group etching grooves 28 are coupled only by the flexible sheet 39.

The present embodiment can achieve same advantages as those in the preceding embodiments.

Note that the transducer elements 25 manufactured by each of the above-described embodiments are each configured such that a rigid body portion of the flexible sheet 39 including the lower electrode 35 has higher rigidity than that of a membrane. For this reason, only the membrane side deforms at the time of electrostatic actuation, ultrasounds can be efficiently transmitted, and strength enough to prevent damage to an element portion when bent is ensured.

A configuration in which a rigid body portion is composed of the lower electrode 35 formed by patterning and an insulating layer has been described in the present embodiment. However, a rigid body portion may be formed using the unpatterned lower electrode 35 alone. In this case, although a parasitic capacitance caused by an increase in electrode area on the signal side increases, same operational advantages can be achieved in terms of functionality.

An example in which one ultrasonic transducer composed of the plurality of transducer elements 25 is mounted at the distal end rigid portion 7 has been described in the present embodiment. However, the present invention is not limited to this. The present invention can also be applied to an example of a biplane type in which two ultrasonic transducers are mounted at the distal end rigid portion 7 or the ultrasonic endoscope I having a plurality of ultrasonic transducers mounted at the distal end rigid portion 7, and same advantages can, of course, be achieved.

The present invention described with reference to the above embodiments is not limited to the embodiments and modifications thereof. In an implementation phase, various modifications can be made without departing from the spirit and scope of the present invention. The above-described embodiments include inventions at various phases, and various inventions can be extracted by an appropriate combination of a plurality of constituent features disclosed.

For example, even if some are deleted from all constituent features disclosed in the embodiments, a configuration having the constituent features deleted can be extracted as an invention when the configuration can solve the problems to be solved by the present invention, and the advantages described above can be achieved.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic endoscope comprising:
an ultrasonic transducer having an ultrasonic transmitting and receiving surface that is bent, the ultrasonic transducer including:
a flexible sheet;
a plurality of transducer elements arranged on an upper surface of the flexible sheet, wherein each of the plurality of transducer elements is a minimum driving unit of the ultrasonic transducer; and
a groove portion formed between adjacent transducer elements of the plurality of transducer elements to reach the flexible sheet, so as to isolate adjacent transducer elements with respect to each other;
wherein, a transducer element of the plurality of transducer elements includes at least one transducer cell, a transducer element of the plurality of transducer elements comprising:
a rigid body portion having a lower side arranged on the upper surface of the flexible sheet such that the flexible sheet is bendable along the groove portion, the rigid body portion comprising a lower electrode,
an insulating partition portion arranged on an upper side of the rigid body portion, the insulating partition portion defining at least one cavity, wherein each of the at least one cavity corresponds to one transducer cell of the transducer element, and
an upper electrode separated by the insulating partition portion from and opposed to the lower electrode.

2. The ultrasonic endoscope according to claim 1, wherein the lower electrode of the rigid body portion is comprised of a thin-film conductive material and one of a thin-film rigid insulator and a thin-film rigid dielectric.

3. The ultrasonic endoscope according to claim 1, wherein the transducer cell is a micromachined capacitive ultrasonic transducer cell.

4. The ultrasonic endoscope according to claim 2, wherein the transducer cell is a micromachined capacitive ultrasonic transducer cell.

5. The ultrasonic endoscope according to claim 1, wherein the rigid body portion is thinner than the flexible sheet.

6. The ultrasonic endoscope according to claim 2, wherein the rigid body portion is thinner than the flexible sheet.

7. The ultrasonic endoscope according to claim 3, wherein the rigid body portion is thinner than the flexible sheet.

8. The ultrasonic endoscope according to claim 4, wherein the rigid body portion is thinner than the flexible sheet.

9. The ultrasonic endoscope according to claim 1, further comprising:
    a membrane portion comprising:
        the upper electrode,
        an upper insulating layer arranged on an upper surface of the upper electrode, and
        an upper protection film arranged on an upper surface of the upper insulating layer,
    wherein the rigid body portion has higher rigidity than the membrane portion.

10. The ultrasonic endoscope according to claim 2, further comprising:
    a membrane portion comprising:
        the upper electrode,
        an upper insulating layer arranged on an upper surface of the upper electrode, and
        an upper protection film arranged on an upper surface of the upper insulating layer,
    wherein the rigid body portion has higher rigidity than the membrane portion.

11. The ultrasonic endoscope according to claim 3, further comprising:
    a membrane portion comprising:
        the upper electrode,
        an upper insulating layer arranged on an upper surface of the upper electrode, and
        an upper protection film arranged on an upper surface of the upper insulating layer,
    wherein the rigid body portion has higher rigidity than the membrane portion.

12. The ultrasonic endoscope according to claim 5, further comprising:
    a membrane portion comprising:
        the upper electrode,
        an upper insulating layer arranged on an upper surface of the upper electrode, and
        an upper protection film arranged on an upper surface of the upper insulating layer,
    wherein the rigid body portion has higher rigidity than the membrane portion.

13. The ultrasonic endoscope according to claim 1, wherein the rigid body portion has a thickness of 3.3 µm or more.

14. The ultrasonic endoscope according to claim 1, wherein:
    the groove portion is formed by etching to reach the flexible sheet, and
    the upper protection film is formed to be a thin film by evaporation.

* * * * *